US012799097B2

(12) United States Patent
Zhang et al.

(10) Patent No.: US 12,799,097 B2
(45) Date of Patent: Nov. 17, 2026

(54) CRYSTALLINE CSF-1R INHIBITOR ACIDIC SALT, PREPARATION METHOD THEREFOR AND USE THEREOF

(71) Applicant: Abbisko Therapeutics Co. Ltd., Pudong New Area (CN)

(72) Inventors: Lei Zhang, Pudong New Area (CN); Baowei Zhao, Pudong New Area (CN); Hongping Yu, Pudong New Area (CN)

(73) Assignee: ABBISKO THERAPEUTICS CO. LTD., Pudong New Area (CN)

( * ) Notice: Subject to any disclaimer, the term of this patent is extended or adjusted under 35 U.S.C. 154(b) by 411 days.

(21) Appl. No.: 18/290,102

(22) PCT Filed: May 23, 2022

(86) PCT No.: PCT/CN2022/094457
§ 371 (c)(1),
(2) Date: Nov. 9, 2023

(87) PCT Pub. No.: WO2022/247786
PCT Pub. Date: Dec. 1, 2022

(65) Prior Publication Data

US 2024/0317710 A1 Sep. 26, 2024

(30) Foreign Application Priority Data

May 24, 2021 (CN) ........................ 202110565750.3

(51) Int. Cl.
*C07D 401/14* (2006.01)
*A61K 31/444* (2006.01)
*A61P 3/00* (2006.01)
*A61P 35/00* (2006.01)
*A61P 37/00* (2006.01)

(52) U.S. Cl.
CPC .................................. *C07D 401/14* (2013.01)

(58) Field of Classification Search
CPC ........................... C07D 401/14; A61K 31/444; C07B 2200/13; A61P 35/00; A61P 3/00; A61P 37/00
See application file for complete search history.

(56) References Cited

U.S. PATENT DOCUMENTS

| | | | |
|---|---|---|---|
| 8,841,455 | B2 | 9/2014 | Boys et al. |
| 11,149,021 | B2 | 10/2021 | Zhao et al. |

FOREIGN PATENT DOCUMENTS

| | | | | |
|---|---|---|---|---|
| EP | 3632907 | A1 | 4/2020 | |
| JP | 2003/519698 | | 6/2003 | |
| JP | 2020520978 | A | 7/2020 | |
| RU | 2562977 | C2 | 9/2015 | |
| WO | WO 2001/051919 | A2 | 7/2001 | |
| WO | 2006067445 | A2 | 6/2006 | |
| WO | 2014145015 | A2 | 9/2014 | |
| WO | 2014145023 | A1 | 9/2014 | |
| WO | 2014145028 | A2 | 9/2014 | |
| WO | WO-2018214867 | A1 * | 11/2018 | ............. A61P 35/00 |

OTHER PUBLICATIONS

English translation of the claims of WO-2018214867-A1, https://translationportal.epo.org/emtp/translate/?ACTION=claims-retrieval&COUNTRY=WO&ENGINE=google&FORMAT=docdb&KIND=A1&LOCALE=en_EP&NUMBER=2018214867&OPS=ops.epo.org/3.2&SRCLANG=zh&TRGLANG=en, Accessed on Jun. 22, 2026. (Year: 2026).*

English translation of the description of WO-2018214867-A1, https://translationportal.epo.org/emtp/translate/?ACTION=description-retrieval&COUNTRY=WO&ENGINE=google&FORMAT=docdb&KIND=A1&LOCALE=en_EP&NUMBER=2018214867&OPS=ops.epo.org/3.2&SRCLANG=zh&TRGLANG=en, Accessed on Jun. 22, 2026. (Year: 2026).*

Bastin et al., "Salt Selection and Optimisation Procedures for Pharmaceutical New Chemical Entities," Organic Process Research & Development, vol. 4, No. 5, pp. 427-435 (2000).

Gupta et al., "Salts of Therapeutic Agents: Chemical, Physiocochemical, and Biological Considerations," Molecules, vol. 23, No. 1719, 15 pages (2018).

(Continued)

*Primary Examiner* — Kamal A Saeed
*Assistant Examiner* — Sagar Patel
(74) *Attorney, Agent, or Firm* — FINNEGAN, HENDERSON, FARABOW, GARRETT & DUNNER, LLP

(57) ABSTRACT

Provided are an acid salt of a crystalline CSF-1R inhibitor, and a preparation method therefor and the use thereof, wherein the CSF-1R inhibitor is the compound 3,3-dimethyl-N-(6-methyl-5-((2-(1-methyl-1H-pyrazol-4-yl)pyridin-4-yl)oxy)pyridin-2-yl)-2-oxopyrrolidine-1-carboxamide having the structure of formula (I). The crystalline acid salt compound can greatly improve the physicochemical properties such as solubility, hygroscopicity and chemical stability of the compound of formula (I) in a free state, and meet the requirements for industrial production and clinical drug preparation development. The crystalline acid salt compound can be widely used in the preparation of a drug for treating cancers, tumors, autoimmune diseases, metabolic diseases or metastatic diseases.

(I)

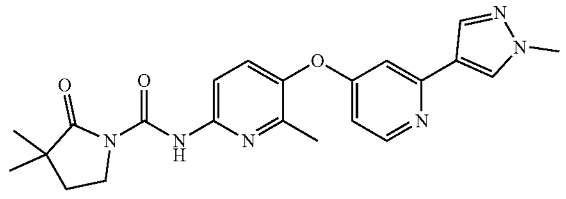

10 Claims, 12 Drawing Sheets

(56) References Cited

OTHER PUBLICATIONS

Office Action and Search Report issued Jun. 24, 2024 in RU Application No. 2023125775/04(056955).
Sarma et al., "Solid forms of pharmaceuticals: Polymorphs, salts and cocrystals," Korean J. Chem. Eng., vol. 28, No. 2, pp. 315-322 (2011).
Variankaval et al., "From Form to Function: Crystallization of Active Pharmaceutical Ingredients", AIChE Journal, vol. 54, No. 7, pp. 1682-1688 (2008).
Bavin, N., "Polymorphism in Process Development," Chemistry & Industry, pp. 527-529 (1989).
Byrn et al., "Pharmaceutical Solids: A Strategic Approach to Regulatory Considerations," Pharmaceutical Research, vol. 12, No. 7, pp. 945-954 (1995).
Carlson et al., "An integrated high throughput workflow for preformulations: Polymorph and salt section studies," Drug Development, pp. 10-15 (2003).
Office Action issued Oct. 2, 2024 in CA Application No. 3211329.
International Search Report and Written Opinion issued Aug. 23, 2022 in PCT/CN2022/094457 (Translation of ISR only).
Balbach et al., "Pharmaceutical evaluation of early development candidates "the 100 mg-approach"", International Journal of Pharmaceutics, vol. 275 , pp. 1-12 (2004).
Caira, M., "Crystalline Polymorphism of Organic Compounds," Topics in Current Chemistry, vol. 198, pp. 163-208 (1998).
Examination Report No. 1 issued on Aug. 15, 2024 in AU Application No. 2022280839.
Singhal et al., "Drug polymorphism and dosage form design: a practical perspective," Advanced Drug Delivery Reviews, vol. 56, pp. 335-347 (2004).
Caira M.R., "Crystalline Polymorphism of Organic Compounds," Topics in Current Chemistry, 1998, vol. 198, pp. 163-208.
Rodriguez-Spong B. et al., "General Principles of Pharmaceutical Solid Polymorphism: a Supramolecular Perspective," Advanced Drug Delivery Reviews, 2004, vol. 56, pp. 241-274.
Kummerer K., "Pharmaceuticals in the Environment," Annual Review of Environment and Resources, 2010, vol. 35, pp. 57-75.
Takata N., "API Form Screening and Selection in Drug Discovery Stage," Pharm Stage, 2007, vol. 6, pp. 20-25.
Examination Report issued Mar. 4, 2026 in JP Application No. 2023572651.
Extended European Search Report issued on Feb. 28, 2025, in EP Application No. 22810511.0.
Serajuddin et al., "Salt formation to improve drug solubility," Advanced Drug Delivery Reviews, vol. 59, pp. 603-616 (2007).
Office Action issued Jul. 22, 2025 in JP Application No. 2023572651.
Ashizawa, K., "Chemistry of Polymorphism and Crystallization of Pharmaceuticals," pp. 273, 278, 305-317 (2002), with English translation.
Office Action issued Nov. 19, 2024 in JP Application No. 2023-572651.

* cited by examiner

CRYSTALLINE CSF-1R INHIBITOR ACIDIC SALT, PREPARATION METHOD THEREFOR AND USE THEREOF

CROSS-REFERENCE TO RELATED APPLICATIONS

This application is a Section 371 of International Application No. PCT/CN2022/094457, filed May 23, 2022, which was published in the Chinese language on Dec. 1, 2022 under International Publication No. WO 2022/247786 A1, which claims priority under 35 U.S.C. § 119 (b) to Chinese Application No. 202110565750.3, filed May 24, 2021, the disclosures of which are incorporated herein by reference in their entireties.

TECHNICAL FIELD

The present invention belongs to the field of medicament development, and particularly relates to a crystalline CSF-1R inhibitor acidic salt, preparation method therefor and use thereof.

BACKGROUND

CSF-1R (cFMS) is short for colony-stimulating factor-1 receptor. CSF-1R, as well as cKIT, FLT3 and PDGFRA&B, belongs to the type III growth hormone receptor family. The receptor is a membrane protein expressed on the surface of macrophages and monocytes. Its extracellular domain is capable of binding to the macrophage colony-stimulating factor, and the intracellular domain tyrosine kinase can activate downstream cell growth and proliferation signal pathways for macrophages and monocytes, including MAPK, PI3K, etc. Therefore, the CSF-1R signal pathway is critical for the development and differentiation of macrophages and monocytes and the physiological function of tumor-associated macrophages (TAMs).

As cancer immunotherapy has advanced in recent years, tumor-associated macrophages (TAMs) and myeloid-derived suppressor cells (MDSCs) are believed to contribute directly to the formation of the immunosuppressive tumor microenvironment and the angiogenesis process supporting tumor growth. Meanwhile, clinical studies have shown that the number of TAMs is negatively correlated with the prognosis of cancer patients. Efficacy studies in mice show that inhibiting the CSF-1R signal pathway can remarkably reduce the number of immunosuppressive macrophages in tumors, and increase the number of CD8-positive T cells. These study results show that CSF-1R small-molecule inhibitors may reverse the immunosuppressive microenvironment in tumors, promote the activation of the immune system, and prolong survival in cancer patients.

During the process of long-term research Abbisko Therapeutics Co., Ltd found a small-molecule compound of a novel structure having the effect of inhibiting CSF-1R (WO2018214867 A1; international publication date: Nov. 29, 2018), a representative compound of which is shown below:

(I)

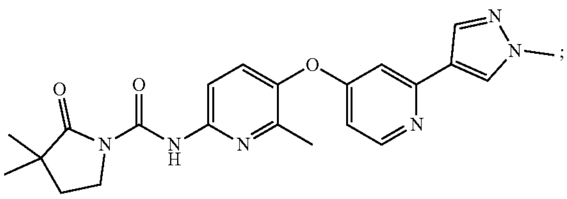

the name is: 3,3-dimethyl-N-(6-methyl-5-((2-(1-methyl-1H-pyrazol-4-yl)pyridin-4-yl)oxy)pyridin-2-yl)-2-oxopyrrolidine-1-carboxamide (compound of formula (I)). The compound can significantly improve the inhibitory effect against the CSF-1R target and the selectivity for other kinase receptors, increase the therapeutic window, reduce clinical toxic and side effects and satisfy the need for targeted therapy for tumors such as lung cancer, breast cancer, prostate cancer, ovarian cancer, cervical cancer, melanoma, pancreatic cancer, head and neck cancer, glioma and giant cell tumor of tendon sheath in China and other countries at this stage.

However, at the time of filing the patent application WO2018214867A1, no further research has been carried out to develop a starting material form suitable for industrial production or a process suitable for industrial application, nor has the state of aggregation of the compound of formula (I) been studied in depth in order to improve the physicochemical properties of the compound and satisfy the requirements of pharmaceutical or clinical applications. WO2018214867A1 discloses an amorphous free-form or foamy solid compound, and the specific preparation method is described in Example 1: The solution of 3,3-dimethyl-2-oxopyrrolidine-1-carbonyl chloride (0.33 mmol) in dichloromethane (10 mL) was added dropwise to the solution of 6-methyl-5-((2-(1-methyl-1H-pyrazol-4-yl)pyridin-4-yl)oxy)pyridin-2-amine (93 mg, 0.33 mmol) and pyridine (78 mg, 0.99 mmol) in dichloromethane (10 mL) under an ice bath. The reaction solution was stirred at 5° C. for 30 min, and then stirred at room temperature for 2 hrs. Dichloromethane and water were added, and then the mixture solution was separated. The organic phase was successively washed with water and a saturated brine, then dried over anhydrous sodium sulfate, filtered, concentrated, and separated by column chromatography [eluent: dichloromethane/methanol (15:1)] to obtain the foamy compound, 3,3-dimethyl-N-(6-methyl-5-((2-(1-methyl-1H-pyrazol-4-yl)pyridin-4-yl)oxy)pyridin-2-yl)-2-oxopyrrolidine-1-carboxamide (42 mg, yield 30.4%). The above foamy compound was identified as an amorphous compound by the inventors. It easily absorbs moisture and softens, cannot be stored and is not suitable for clinical formulation development. Therefore, in order to satisfy the needs of clinical research and the launch of drug formulations, there is an urgent need to develop an aggregate form suitable for medicament development to overcome the defects in the prior art.

SUMMARY

In order to solve the problems in the prior art, the inventors studied in depth various aggregate forms of the compound of formula (I) (3,3-dimethyl-N-(6-methyl-5-((2-(1-methyl-1H-pyrazol-4-yl)pyridin-4-yl)oxy)pyridin-2-yl)-2-oxopyrrolidine-1-carboxamide) and developed a number of crystalline acidic salts, particularly a hydrochloride, which greatly improve the physicochemical properties, such as solubility, hygroscopicity and chemical stability, of the compound of formula (I). The material of crystalline acidic salt compound meets the requirements of industrial production and can satisfy the needs of clinical medicament formulation development. The crystalline acidic salt compounds are of great clinical application value and are expected to accelerate the development of a new generation of CSF-1R small-molecule inhibitors.

The first aspect of the present invention provides a crystalline acidic salt of the compound of formula (I):

(I)

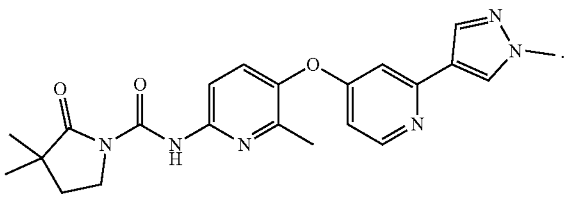

As a preferred embodiment, the crystalline acidic salt of the compound of formula (I) is an inorganic acid salt or an organic acid salt.

As a further preferred embodiment, the crystalline acidic salt of the compound of formula (I) is an inorganic acid salt selected from the group consisting of hydrochloride, sulfate, hydrobromide, hydrofluoride, hydroiodide and phosphate.

As a further preferred embodiment, the crystalline acidic salt of the compound of formula (I) is an organic acid salt selected from the group consisting of acetate, dichloroacetate, trichloroacetate, trifluoroacetate, benzenesulfonate, p-toluenesulfonate, 4-chlorobenzenesulfonate, 1,5-naphthalenedisulfonate, naphthalene-2-sulfonate, ethane-1,2-disulfonate, methanesulfonate, ethanesulfonate, benzoate, decanoate, hexanoate, octanoate, cinnamate, citrate, cyclohexane aminosulfonate, camphorsulfonate, aspartate, camphorate, gluconate, glucuronate, glutamate, isoascorbate, lactate, malate, mandelate, pyroglutamate, tartrate, dodecylsulfate, dibenzoyltartrate, formate, fumarate, galactonate, gentisate, acetohydroxamate, malonate, succinate, glutarate, adipate, sebacate, 2-ketoglutarate, glycolate, hippurate, isethionate, lactobionate, ascorbate, aspartate, laurate, maleate, nicotinate, oleate, orotate, oxalate, palmitate, pamoate, propionate, 4-acetamidobenzoate, 4-aminobenzoate, salicylate, 4-aminosalicylate, 2,5-dihydroxybenzoate, 1-hydroxy-2-naphthoate, stearate, thiocyanate, undecylenate and succinate.

As a more further preferred embodiment, the crystalline acidic salt of the compound of formula (I) is an organic acid salt selected from methanesulfonate, citrate, malate, fumarate and tartrate.

As a more further preferred embodiment, the crystalline acidic salt of the compound of formula (I) is a hydrochloride, an X-ray powder diffraction (XRPD) pattern of which comprises four or more peaks at angles of diffraction (2θ) of 9.52±0.2°, 19.72±0.2°, 10.64±0.2°, 14.32±0.2°, 16.56±0.2°, 18.52±0.2° and 27.2°+0.2°.

As the most preferred embodiment, the crystalline acidic salt of the compound of formula (I) is a hydrochloride, an X-ray powder diffraction pattern of which comprises peaks which are substantially identical (±0.2°) to those at angles of diffraction (2θ) shown in FIG. 1; the X-ray powder diffraction data are shown in Table 1:

| 2θ (°) | Intensity % | 2θ (°) | Intensity % |
|---|---|---|---|
| 9.52 | 100 | 27.20 | 39 |
| 19.72 | 77.4 | 25.88 | 29.1 |
| 10.64 | 50.3 | 21.40 | 25.5 |
| 14.32 | 50 | 24.00 | 19.5 |
| 16.56 | 43.2 | 23.54 | 19.3 |
| 18.52 | 39 | 28.92 | 18.8 |
| 30.92 | 16.6 | 24.92 | 15.1 |
| 13.50 | 15.9 | 27.66 | 10 |
| 17.22 | 15.2 | 32.40 | 9.8 |

This crystalline hydrochloride is designated hydrochloride crystalline form I and has a melting point of 157.8° C.

As a more further preferred embodiment, the crystalline acidic salt of the compound of formula (I) is a hydrochloride, an X-ray powder diffraction (XR-PD) pattern of which comprises four or more peaks at angles of diffraction (2θ) of 24.32±0.2°, 17.78±0.2°, 24.58±0.2°, 19.96±0.2°, 10.18±0.2°, 21.34±0.2°, 18.06±0.2°, 28.10±0.2° and 18.42±0.28.

As the most preferred embodiment, the crystalline acidic salt of the compound of formula (I) is a hydrochloride, an X-ray powder diffraction pattern of which comprises peaks which are substantially identical (±0.2°) to those at angles of diffraction (2θ) shown in FIG. 2; the X-ray powder diffraction data are shown in Table 2:

| 2θ (°) | Intensity % | 2θ (°) | Intensity % |
|---|---|---|---|
| 24.32 | 100 | 18.06 | 44.9 |
| 17.78 | 76 | 28.10 | 41.3 |
| 24.58 | 75.6 | 18.42 | 40.9 |
| 19.96 | 49.7 | 25.26 | 31.8 |
| 10.18 | 47.9 | 8.26 | 31 |
| 21.34 | 47.2 | 28.58 | 26.8 |
| 13.92 | 19 | 15.88 | 13.8 |
| 16.50 | 19 | 11.90 | 13.1 |
| 14.92 | 14 | 20.38 | 12.6 |

This crystalline hydrochloride is designated hydrochloride crystalline form II and has a melting point of 120.6° C.

As a more further preferred embodiment, the crystalline acidic salt of the compound of formula (I) is a hydrochloride, an X-ray powder diffraction (XR-PD) pattern of which comprises four or more peaks at angles of diffraction (2θ) of 18.74±0.2°, 22.94±0.2°, 17.64±0.2°, 9.38±0.2°, 9.10±0.2°, 9.94±0.2°, 29.70±0.2° and 11.24±0.2°.

As the most preferred embodiment, the crystalline acidic salt of the compound of formula (I) is a hydrochloride, an X-ray powder diffraction pattern of which comprises peaks which are substantially identical (±0.2°) to those at angles of diffraction (2θ) shown in FIG. 3; the X-ray powder diffraction data are shown in Table 3:

| 2θ (°) | Intensity % | 2θ (°) | Intensity % |
|---|---|---|---|
| 18.74 | 100 | 29.70 | 31.4 |
| 22.94 | 87.2 | 11.24 | 30.7 |
| 17.64 | 72.5 | 8.78 | 23.8 |
| 9.38 | 71 | 27.00 | 22.2 |

-continued

| 2θ (°) | Intensity % | 2θ (°) | Intensity % |
|---|---|---|---|
| 9.10 | 62 | 26.54 | 18.5 |
| 9.94 | 35.3 | 35.76 | 13.4 |
| 28.28 | 12.5 | 34.34 | 11.3 |
| 33.20 | 11.8 | 30.12 | 11 |
| 14.66 | 11.7 | 21.16 | 10.4 |

This crystalline hydrochloride is designated hydrochloride crystalline form III and has a melting point of 110.9° C.

As a more further preferred embodiment, the crystalline acidic salt of the compound of formula (I) is a sulfate, an X-ray powder diffraction (XR-PD) pattern of which comprises four or more peaks at angles of diffraction (2θ) of 20.08±0.2°, 23.22±0.2°, 21.38±0.2°, 24.86±0.2°, 18.78±0.2, 20.46±0.2 and 9.38±0.2°.

As the most preferred embodiment, the crystalline acidic salt of the compound of formula (I) is a sulfate, an X-ray powder diffraction pattern of which comprises peaks which are substantially identical (±0.2°) to those at angles of diffraction (2θ) shown in FIG. 4; the X-ray powder diffraction data are shown in Table 4:

| 2θ (°) | Intensity % | 2θ (°) | Intensity % |
|---|---|---|---|
| 20.08 | 100 | 9.38 | 53.8 |
| 23.22 | 86.6 | 26.88 | 44 |
| 21.38 | 77 | 17.12 | 43.5 |
| 24.86 | 70.9 | 29.30 | 27.1 |
| 18.78 | 60.2 | 16.64 | 24.3 |
| 20.46 | 56.9 | 18.12 | 20.5 |
| 24.06 | 20 | 8.78 | 18 |
| 24.48 | 19.3 | 19.34 | 18 |
| 28.14 | 18.8 | 13.97 | 17.5 |

The crystalline sulfate is designated sulfate crystalline form I.

As a more further preferred embodiment, the crystalline acidic salt of the compound of formula (I) is a phosphate, an X-ray powder diffraction (XR-PD) pattern of which comprises four or more peaks at angles of diffraction (2θ) of 8.44±0.2°, 16.82±0.2°, 10.78±0.2°, 18.10±0.2°, 24.78±0.2°, 19.62±0.2° and 23.24±0.2°.

As the most preferred embodiment, the crystalline acidic salt of the compound of formula (I) is a phosphate, an X-ray powder diffraction pattern of which comprises peaks which are substantially identical (±0.2°) to those at angles of diffraction (2θ) shown in FIG. 5; the X-ray powder diffraction data are shown in Table 5:

| 2θ (°) | Intensity % | 2θ (°) | Intensity % |
|---|---|---|---|
| 8.44 | 100 | 23.24 | 22.1 |
| 16.82 | 66.2 | 21.36 | 19.9 |
| 10.78 | 53.2 | 27.44 | 17.7 |
| 18.10 | 41.8 | 15.90 | 17.2 |
| 24.78 | 24.6 | 23.58 | 15.6 |
| 19.62 | 22.1 | 11.68 | 15.4 |
| 21.76 | 15.1 | 26.12 | 12.5 |
| 27.92 | 14.3 | 20.36 | 10.8 |
| 25.42 | 13.7 | 15.26 | 9.4 |

This crystalline phosphate is designated phosphate crystalline form I and has a melting point of 154.2° C.

As a more further preferred embodiment, the crystalline acidic salt of the compound of formula (I) is a phosphate, an X-ray powder diffraction (XR-PD) pattern of which comprises four or more peaks at angles of diffraction (2θ) of 10.86±0.2°, 8.48±0.2°, 17.02±0.2, 10.46±0.2°, 18.38±0.2°, 7.98±0.2°, 23.82±0.2° and 16.06±0.2.

As the most preferred embodiment, the crystalline acidic salt of the compound of formula (I) is a phosphate, an X-ray powder diffraction pattern of which comprises peaks which are substantially identical (±0.2°) to those at angles of diffraction (2θ) shown in FIG. 6; the X-ray power diffraction data are shown in Table 6:

| 2θ (°) | Intensity % | 2θ (°) | Intensity % |
|---|---|---|---|
| 10.86 | 100 | 23.82 | 33.3 |
| 8.48 | 90.6 | 16.06 | 32.7 |
| 17.02 | 90.2 | 22.34 | 31.8 |
| 10.46 | 42.3 | 11.76 | 30.9 |
| 18.38 | 36.9 | 13.82 | 30.9 |
| 7.98 | 35.5 | 27.96 | 28.8 |
| 12.10 | 26.5 | 25.02 | 21.7 |
| 21.54 | 25.2 | 19.94 | 21.3 |
| 19.06 | 22.1 | 17.52 | 20.2 |

This crystalline phosphate is designated phosphate crystalline form II and has a melting point of 153.8° C.

As a more further preferred embodiment, the crystalline acidic salt of the compound of formula (I) is a phosphate, an X-ray powder diffraction (XR-PD) pattern of which comprises four or more peaks at angles of diffraction (2θ) of 10.84±0.2°, 8.54±0.2°, 17.14±0.2°, 16.76±0.2°, 10.36±0.2°, 18.26±0.2°, 27.88±0.2° and 22.34±0.2°.

As the most preferred embodiment, the crystalline acidic salt of the compound of formula (I) is a phosphate, an X-ray powder diffraction pattern of which comprises peaks which are substantially identical (±0.2°) to those at angles of diffraction (2θ) shown in FIG. 7; the X-ray powder diffraction data are shown in Table 7:

| 2θ (°) | Intensity % | 2θ (°) | Intensity % |
|---|---|---|---|
| 10.84 | 100 | 27.88 | 22.2 |
| 8.54 | 44.4 | 22.34 | 20.3 |
| 17.14 | 32.8 | 25.06 | 17.6 |
| 16.76 | 27.4 | 23.70 | 17.1 |
| 10.36 | 24.7 | 13.78 | 16.2 |
| 18.26 | 23.9 | 11.68 | 16.1 |
| 16.04 | 13.1 | 26.14 | 9.5 |
| 20.10 | 12.7 | 21.08 | 9.1 |
| 19.34 | 11.8 | 12.08 | 8.7 |

This crystalline phosphate is designated phosphate crystalline form III and has a melting point of 147.3° C.

As a more further preferred embodiment, the crystalline acidic salt of the compound of formula (I) is a methanesulfonate, an X-ray powder diffraction (XR-PD) pattern of which comprises four or more peaks at angles of diffraction (2θ) of 16.28±0.2°, 20.82±0.2°, 7.78±0.2°, 26.68±0.2°, 23.36±0.2°, 26.30±0.2° and 23.62±0.2°.

As the most preferred embodiment, the crystalline acidic salt of the compound of formula (I) is a methanesulfonate, an X-ray powder diffraction pattern of which comprises peaks which are substantially identical (±0.2°) to those at angles of diffraction (2θ) shown in FIG. 8; the X-ray powder diffraction data are shown in Table 8:

| 2θ (°) | Intensity % | 2θ (°) | Intensity % |
|---|---|---|---|
| 16.28 | 100 | 23.62 | 27.8 |
| 20.82 | 42 | 10.74 | 20.7 |
| 7.78 | 39.2 | 19.54 | 20.4 |
| 26.68 | 36.5 | 13.72 | 20.2 |
| 23.36 | 33.2 | 18.40 | 18.5 |
| 26.30 | 29.3 | 22.34 | 17.2 |
| 8.54 | 14.8 | 15.34 | 8.5 |
| 25.96 | 9 | 17.54 | 7.4 |
| 27.72 | 8.6 | 12.44 | 6.3 |

This crystalline methane sulfonate is designated methane sulfonate crystalline form I and has a melting point of 184.4° C.

As a more further preferred embodiment, the crystalline acidic salt of the compound of formula (I) is a methane-sulfonate, an X-ray powder diffraction (XR-PD) pattern of which comprises four or more peaks at angles of diffraction (2θ) of 8.64±0.2°, 21.02±0.2°, 16.34±0.2°, 23.34±0.2°, 18.48±0.2°, 7.84±0.2°, 26.00±0.2° and 10.82±0.2°.

As the most preferred embodiment, the crystalline acidic salt of the compound of formula (I) is a methanesulfonate, an X-ray powder diffraction pattern of which comprises peaks which are substantially identical (±0.2°) to those at angles of diffraction (2θ) shown in FIG. 9; the X-ray powder diffraction data are shown in Table 9:

| 2θ (°) | Intensity % | 2θ (°) | Intensity % |
|---|---|---|---|
| 8.64 | 100 | 10.82 | 32 |
| 21.02 | 82.6 | 26.74 | 30.6 |
| 16.34 | 68.4 | 23.66 | 28.5 |
| 23.34 | 58.8 | 19.52 | 27.8 |
| 18.48 | 51.4 | 12.96 | 24.6 |
| 7.84 | 38.3 | 26.34 | 23.8 |
| 26.00 | 32.7 | 20.04 | 22.1 |
| 17.32 | 18.2 | 17.56 | 15.8 |
| 22.34 | 18.1 | 15.00 | 15.6 |
| 24.58 | 16.3 | 30.20 | 15.3 |

This crystalline methanesulfonate is designated methane sulfonate crystalline form II and has a melting point of 185.5° C.

As a more further preferred embodiment, the crystalline acidic salt of the compound of formula (I) is a citrate, an X-ray powder diffraction (XR-PD) pattern of which comprises four or more peaks at angles of diffraction (2θ) of 16.14±0.2°, 7.12±0.2°, 14.86±0.2°, 16.64±0.2°, 21.34±0.21 and 13.70±0.2°.

As the most preferred embodiment, the crystalline acidic salt of the compound of formula (I) is a citrate, an X-ray powder diffraction pattern of which comprises peaks which are substantially identical (±0.2°) to those at angles of diffraction (2θ) shown in FIG. 10; the X-ray powder diffraction data are shown in Table 10:

| 2θ (°) | Intensity % | 2θ (°) | Intensity % |
|---|---|---|---|
| 16.14 | 100 | 13.70 | 31.7 |
| 7.12 | 96.1 | 18.34 | 26.2 |
| 14.86 | 83 | 14.24 | 22 |
| 16.64 | 76.9 | 8.04 | 18.7 |
| 21.34 | 39.8 | 17.64 | 15.4 |
| 26.50 | 14 | 28.44 | 11.4 |
| 5.88 | 11.8 | 9.44 | 10.1 |
| 23.08 | 11.6 | 25.38 | 9.8 |

This crystalline citrate is designated citrate crystalline form I and has a melting point of 58.1° C.

As a more further preferred embodiment, the crystalline acidic salt of the compound of formula (I) is a malate, an X-ray powder diffraction (XR-PD) pattern of which comprises four or more peaks at angles of diffraction (2θ) of 8.44±0.2°, 27.82±0.2°, 14.22±0.2°, 9.72±0.2°, 15.44±0.2°, 18.96±0.2° and 19.28±0.2°.

As the most preferred embodiment, the crystalline acidic salt of the compound of formula (I) is a malate, an X-ray powder diffraction pattern of which comprises peaks which are substantially identical (±0.2°) to those at angles of diffraction (2θ) shown in FIG. 11; the X-ray powder diffraction data are shown in Table 11:

| 2θ (°) | Intensity % | 2θ (°) | Intensity % |
|---|---|---|---|
| 8.44 | 100 | 19.28 | 67.1 |
| 27.82 | 99.8 | 17.64 | 31.9 |
| 14.22 | 95.1 | 12.58 | 23.9 |
| 9.72 | 93.2 | 7.61 | 21.4 |
| 15.44 | 72.4 | 16.20 | 21 |
| 18.96 | 69.1 | 21.22 | 18.5 |
| 22.38 | 13.3 | 24.32 | 9 |
| 17.24 | 12.3 | 25.38 | 7.7 |
| 21.98 | 11.7 | 20.88 | 6.5 |

This crystalline malate is designated malate crystalline form I and has a melting point of 82.8° C.

As a more further preferred embodiment, the crystalline acidic salt of the compound of formula (I) is a tartrate, an X-ray powder diffraction (XR-PD) pattern of which comprises four or more peaks at angles of diffraction (2θ) of 9.16±0.2°, 16.64±0.2°, 19.80±0.2°, 26.84±0.2°, 18.96±0.2, 24.06±0.2° and 12.16±0.21.

As the most preferred embodiment, the crystalline acidic salt of the compound of formula (I) is a tartrate, an X-ray powder diffraction pattern of which comprises peaks which are substantially identical (±0.2°) to those at angles of diffraction (2θ) shown in FIG. 12; the X-ray powder diffraction data are shown in Table 12:

| 2θ (°) | Intensity % | 2θ (°) | Intensity % |
|---|---|---|---|
| 9.16 | 100 | 12.16 | 40.8 |
| 16.64 | 86.7 | 18.36 | 34.3 |
| 19.80 | 58.1 | 20.44 | 31 |
| 26.84 | 51.2 | 21.56 | 30.8 |
| 18.96 | 50.1 | 25.02 | 30.7 |
| 24.06 | 48.4 | 8.34 | 25.4 |
| 22.14 | 24.1 | 14.26 | 18 |
| 27.40 | 22.3 | 25.32 | 17.2 |
| 32.66 | 21.8 | 24.40 | 15.3 |

This crystalline tartrate is designated tartrate crystalline form I and has a melting point of 122.4° C.

As a more further preferred embodiment, the crystalline acidic salt of the compound of formula (I) is a fumarate, an X-ray powder diffraction (XR-PD) pattern of which comprises four or more peaks at angles of diffraction (2θ) of 16.82±0.2°, 18.28±0.2°, 11.62±0.2°, 15.10±0.2°, 8.44±0.2°, 21.54±0.2° and 27.58±0.2°.

As the most preferred embodiment, the crystalline acidic salt of the compound of formula (I) is a fumarate, an X-ray powder diffraction pattern of which comprises peaks which are substantially identical (±0.2°) to those at angles of diffraction (2θ) shown in FIG. 13; the X-ray powder diffraction data are shown in Table 13:

| 2θ (°) | Intensity % | 2θ (°) | Intensity % |
|---|---|---|---|
| 16.82 | 100 | 27.58 | 31.8 |
| 18.28 | 69.3 | 25.84 | 29.1 |
| 11.62 | 62.8 | 10.68 | 28.5 |
| 15.10 | 53.5 | 13.06 | 25.8 |
| 8.44 | 48.1 | 24.86 | 23.5 |
| 21.54 | 36.1 | 20.12 | 19 |
| 8.86 | 18.5 | 24.32 | 16.8 |
| 9.98 | 18.3 | 17.16 | 15.7 |
| 25.28 | 17.3 | 27.98 | 15 |

The crystalline fumarate is designated fumarate crystalline form I.

The second aspect of the present invention provides a preparation method for an aforementioned crystalline acidic salt of the compound of formula (I), which comprises the following steps:

1) dissolving or dispersing the compound of formula (I) in free form in a water-containing solvent or a suitable organic solvent, and adding a liquid inorganic or organic acid or solution of acid in solid form to the above system; or adding the compound of formula (I) in free form to a solution of an acid; and
2) collecting a solid product precipitated in the above salt forming reaction process, or creating a degree of supersaturation of the salt forming system to obtain a crystalline product;

the inorganic acid is selected from the group consisting of hydrochloric acid, sulfuric acid, hydrobromic acid, hydrofluoric acid, hydroiodic acid and phosphoric acid; the organic acid salt is selected from the group consisting of acetic acid, dichloroacetic acid, trichloroacetic acid, trifluoroacetic acid, benzenesulfonic acid, p-toluenesulfonic acid, 4-chlorobenzenesulfonic acid, 1,5-naphthalenedisulfonic acid, naphthalene-2-sulfonic acid, ethane-1,2-disulfonic acid, methanesulfonic acid, ethanesulfonic acid, benzoic acid, decanoic acid, hexanoic acid, octanoic acid, cinnamic acid, citric acid, cyclohexane aminosulfonic acid, camphorsulfonic acid, aspartic acid, camphoric acid, gluconic acid, glucuronic acid, glutamic acid, isoascorbic acid, lactic acid, malic acid, mandelic acid, pyroglutamic acid, tartaric acid, dodecylsulfuric acid, dibenzoyltartaric acid, formic acid, fumaric acid, galactonic acid, gentisic acid, acetohydroxamic acid, malonic acid, succinic acid, glutaric acid, adipic acid, sebacic acid, 2-ketoglutaric acid, glycolic acid, hippuric acid, isethionic acid, lactobionic acid, ascorbic acid, lauric acid, maleic acid, nicotinic acid, oleic acid, orotic acid, oxalic acid, palmitic acid, pamoic acid, propionic acid, 4-acetamidobenzoic acid, 4-aminobenzoic acid, salicylic acid, 4-aminosalicylic acid, 2,5-dihydroxybenzoic acid, 1-hydroxy-2-naphthoic acid, stearic acid, thiocyanic acid, undecylenic acid and succinic acid.

As a preferred embodiment, the organic acid is selected from methanesulfonic acid, citric acid, malic acid, fumaric acid and tartaric acid.

As a further preferred embodiment, a method of creating the degree of supersaturation of the salt forming system in step 2) of the preparation method includes one or more of: adding a seed crystal, volatilizing a solvent, adding an anti-solvent and cooling, to obtain the crystalline acidic salt of the compound of formula (I).

As a further preferred embodiment, the suitable organic solvent in the salt forming process of step 1) of the preparation method is selected from the group consisting of alcohols, chloroalkanes, ketones, ethers, cyclic ethers, esters, alkanes, cycloalkanes, benzenes, amides, sulfoxides and mixtures thereof, and aqueous solutions thereof.

As a more further preferred embodiment, the suitable organic solvent in the salt forming process of step 1) of the preparation method is selected from the group consisting of methanol, ethanol, n-propanol, isopropanol, dichloromethane, acetonitrile, acetone, 1,4-dioxane, tetrahydrofuran, N,N-dimethylformamide, ethyl acetate, isopropyl acetate, methyl tert-butyl ether, 2-methoxyethyl ether and a mixture thereof, and an aqueous solution thereof.

The third aspect of the present invention provides a preparation method for an aforementioned crystalline acidic salt of the compound of formula (I), which comprises the following step: converting one crystalline form of the acidic salt of the compound of formula (I) to another crystalline form of the salt by using a crystalline form conversion method, wherein the crystalline form conversion method includes heating or suspension crystalline form conversion in a suitable solvent.

As a further preferred embodiment, the suitable solvent is selected from the group consisting of methanol, ethanol, n-propanol, isopropanol, dichloromethane, acetonitrile, acetone, 1,4-dioxane, tetrahydrofuran, N,N-dimethylformamide, ethyl acetate, isopropyl acetate, methyl tert-butyl ether, 2-methoxyethyl ether and a mixture thereof, and an aqueous solution thereof.

The fourth aspect of the present invention provides a pharmaceutical composition comprising an aforementioned crystalline acidic salt of the compound of formula (I) and a pharmaceutically acceptable carrier.

The fifth aspect of the present invention provides use of an aforementioned crystalline acidic salt of the compound of formula (I) in the preparation of a medicament for treating CSF-1R-associated cancer, tumor, autoimmune disease, metabolic disease or metastatic disease.

The sixth aspect of the present invention provides an aforementioned crystalline acidic salt of the compound of formula (I) for use as a medicament for treating CSF-1R-associated cancer, tumor, autoimmune disease, metabolic disease or metastatic disease.

The seventh aspect of the present invention provides an aforementioned crystalline acidic salt of the compound of formula (I) for use as a medicament for treating CSF-1R-associated ovarian cancer, pancreatic cancer, prostate cancer, lung cancer, breast cancer, renal carcinoma, liver cancer, cervical cancer, metastatic cancer in bone, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, primary tumor metastasis, myeloproliferative disease, leukemia, rheumatic arthritis, rheumatoid arthritis, osteoarthritis, multiple sclerosis, autoimmune nephritis, lupus, Crohn's disease, asthma, chronic obstructive pulmonary disease, osteoporosis, hypereosinophilic syndrome, mastocytosis or mast cell leukemia.

As a preferred embodiment, an aforementioned crystalline acidic salt of the compound of formula (I) is used as a medicament for treating CSF-1R-associated ovarian cancer, pancreatic cancer, prostate cancer, breast cancer, cervical cancer, glioblastoma, multiple myeloma, metabolic disease, neurodegenerative disease, primary tumor metastasis or metastatic cancer in bone.

The eighth aspect of the present invention provides a treatment method for CSF-1R-associated cancer, tumor, autoimmune disease, metabolic disease or metastatic disease, which comprises administering to a patient in need thereof an aforementioned crystalline acidic salt of the compound of formula (I).

BRIEF DESCRIPTION OF THE DRAWINGS

FIG. 1θ shows an X-ray powder diffraction pattern of citrate crystalline form I of the compound of formula (I) of the present invention. The abscissa represents the value of 2θ (degrees), and the ordinate represents peak intensity.

DETAILED DESCRIPTION OF THE INVENTION

Figure 1:
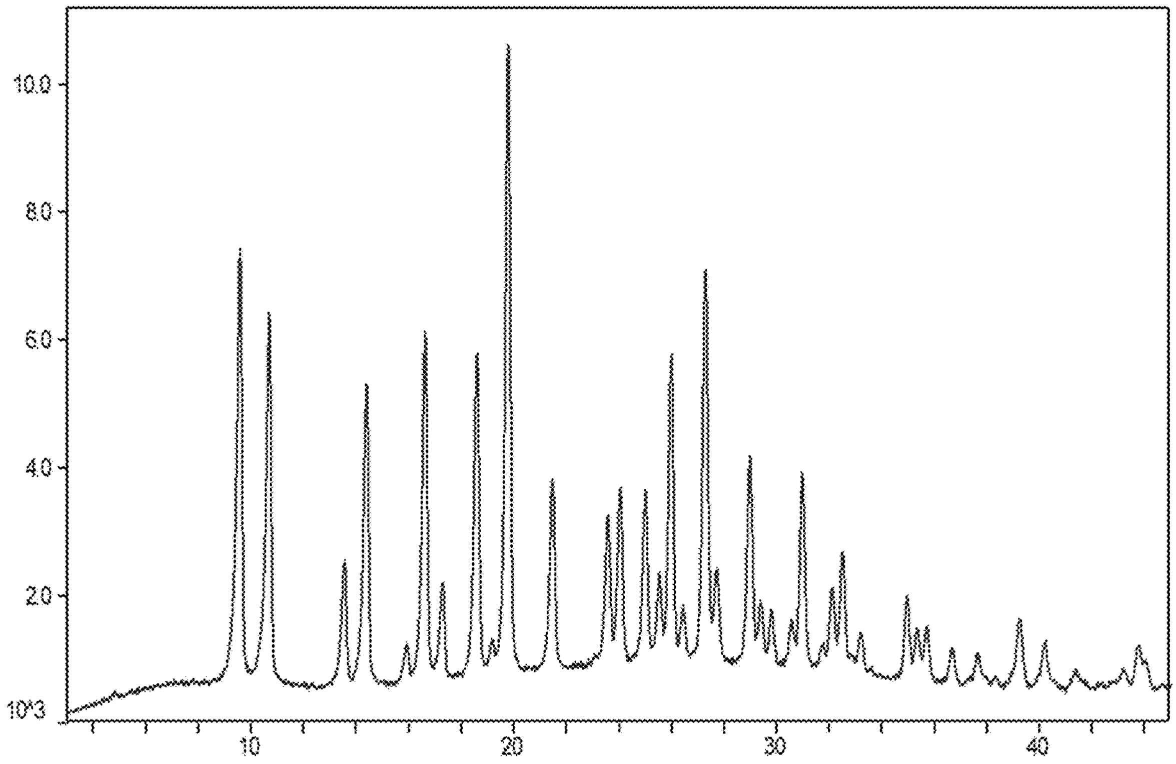
FIG. 1 shows an X-ray powder diffraction pattern of hydrochloride crystalline form I of the compound of formula (I) of the present invention. The abscissa represents the value of 2θ (degrees), and the ordinate represents peak intensity.

The inventors of the present invention studied various aggregate forms of the compound of formula (I), 3,3-dimethyl-N-(6-methyl-5-((2-(1-methyl-1H-pyrazol-4-yl)pyridin-4-yl)oxy)pyridin-2-yl)-2-oxopyrrolidine-1-carboxamide, and provide a crystalline CSF-1R inhibitor acidic salt, which greatly improves the physicochemical properties, such as solubility, hygroscopicity and chemical stability, of the compound of formula (I), so that the crystalline acidic salt can satisfy the needs of clinical medicament formulation development. The crystalline acidic salt is of great clinical application value and can be widely applied to the preparation of a medicament for treating cancer, tumor, autoimmune disease, metabolic disease or metastatic disease, particularly a medicament for treating ovarian cancer, pancreatic cancer, prostate cancer, breast cancer, cervical cancer, glioblastoma, multiple myeloma, metabolic disease, neurodegenerative disease, primary tumor metastasis or metastatic cancer in bones. It is expected to accelerate the development of a new generation of CSF-1R inhibitor medicaments. The present invention is achieved on this basis.

Detailed description: unless otherwise stated, the following terms used in the specification and claims have the following meanings.

"Pharmaceutical composition" refers to a mixture containing one or more of the compounds described herein or a physiologically/pharmaceutically acceptable salt or pro-medicament thereof, and other chemical components, for example physiologically/pharmaceutically acceptable carriers and excipients. The purpose of the pharmaceutical composition is to promote the administration to an organism, which facilitates the absorption of the active ingredient, thereby exerting biological activities.

The compound of formula (I) has a variety of separated acidic salts, showing polymorphism or monomorphism. For example, each of the hydrochloride, phosphate and methanesulfonate is shown as a polymorph; each of the sulfate, citrate, malate, fumarate and tartrate is shown as a monomorph. These "polymorphs" differ in X-ray powder diffraction pattern, physicochemical and pharmacokinetic properties and thermodynamic stability.

As used herein, "salt" refers to a compound prepared by reacting an organic acid or base medicament with a pharmaceutically acceptable inorganic or organic acid or base.

Methods and Materials

The crystalline acidic salts of the compound of formula (I) are characterized by X-ray powder diffraction patterns. Thus, X-ray powder diffraction patterns of the salts were collected on a Rigaku Ultima IV powder diffractometer operating in reflection mode and using Cu Kα radiation. The diffractometer used Cu Kα irradiation (40 kV, 40 mA) and operated at room temperature with a D/tex Ultra detector. The scan range was from 3° to 450 in 20 with a scan rate of 20°/min. The diffraction patterns were analyzed using Jade 5 software (version 5.0.37) released in 2017 by Materials Data, Inc.

XRPD samples were prepared as follows: a sample was placed on a monocrystalline silicon wafer, and the sample powder was pressed with a glass slide or an equivalent to ensure that the sample has a flat surface and a proper height. The sample holder was then placed in the Rigaku Ultima IV XRPD instrument and an X-ray powder diffraction pattern was collected using the instrument parameters described above. Measurement differences associated with such X-ray powder diffraction analyses result from a variety of factors including: (a) errors in sample preparation (e.g., sample height), (b) instrument errors, (c) calibration errors, (d) operator errors (including those errors present when determining peak positions), and (e) the nature of the material (e.g., preferred orientation errors). Calibration errors and sample height errors often result in a shift of all the peaks in the same direction. In general, this calibration factor will bring the measured peak positions into an agreement with the expected peak positions and may be in the range of the expected 2θ value±0.2°. The angle 2θ values (°) and intensity values (as a % of the value of the highest peak) for each polymorph obtained in the examples of the present invention are shown in Tables 1-13.

The experimental method of characterizing the crystalline acidic salts of the compound of formula (I) using differential scanning calorimetry (DSC) is as follows: a small amount of crystalline acidic salt powder of the compound of formula (I) was placed in an aluminum pan that came with the instrument and could be covered with a lid; after the sample was loaded, the aluminum pan was covered with a lid and then sent into the instrument for analysis. In the present patent, all the instruments used for differential scanning calorimetry were TA Q2000, the scanning parameter was set to using nitrogen atmosphere, and the warming rate was 10° C./min.

The experimental method of characterizing the crystalline acidic salts of the compound of formula (I) using thermogravimetric analysis (TGA) is as follows: a small amount of crystalline acidic salt powder of the compound of formula (I) was placed in an aluminum pan that came with the instrument; after the sample was loaded, the aluminum pan was sent into the instrument for analysis. In the present patent, all the instruments used for thermogravimetric analysis were TA Q500, the scanning parameter was set to using nitrogen atmosphere, and the warming rate was 10° C./min.

The experimental method of characterizing the crystalline acidic salts of the compound of formula (I) using dynamic vapor sorption (DVS) is as follows: a small amount of crystalline acidic salt powder of the compound of formula (I) was placed in a precision sample pan that came with the instrument; after the sample was loaded, the aluminum pan was sent into the instrument for analysis. In the present patent, the instruments used for dynamic vapor sorption were all the DVS Intrinsic model, the experimental parameter was set to using nitrogen as a carrier gas, the constant temperature was set to 25° C., the rate of mass percentage change over a unit of time (dm/dt)=0.01%/min was used as a criterion for determining if an equilibrium is reached, and the program humidity change cycle was set as follows: the initial relative humidity was 0%, the relative humidity was 90% at the end of the cycle, 2 cycles were set, and each 10% R.H. change was a step.

The reagents in the examples of the present invention are known and commercially available, or can be synthesized using or according to methods known in the art. The material of API was prepared according to patent WO2018214867A1.

Unless otherwise stated, all reactions of the present invention were carried out under a dry nitrogen or argon atmosphere with continuous magnetic stirring, the solvent was a dry solvent, and the temperature was in degree centigrade (° C.).

Unless otherwise specified, each of the various crystalline forms referred to in the present invention may be an anhydrous crystalline form or a hydrated crystalline form. For example, it is a hydrated crystalline form; preferably, each molecule of the crystal contains 1, 2, 3, 4 or 5 waters of crystallization; more preferably, each molecule of the crystal contains 1 or 2 waters of crystallization.

The present invention is further explained in detail using the drawings and the following examples, which are intended to illustrate specific embodiments of the present invention only and should not be construed as limiting the scope of the present invention in any way.

PREPARATION OF SPECIFIC EXAMPLES

Example 1. Preparation of Hydrochloride Crystalline Form I

About 10 mg of the compound of formula (I) was dissolved in 0.5 mL of methyl tert-butyl ether, and 2.35 μL of concentrated hydrochloric acid in 0.1 mL of methyl tert-butyl ether was added; the mixture was stirred at room temperature for 3 days and filtered, and the filter cake was dried in a drying oven at 50° C. and subjected to an XRPD analysis. The X-ray powder diffraction pattern is shown in FIG. 1.

Example 2. Preparation of Hydrochloride Crystalline Form II

Figure 2:
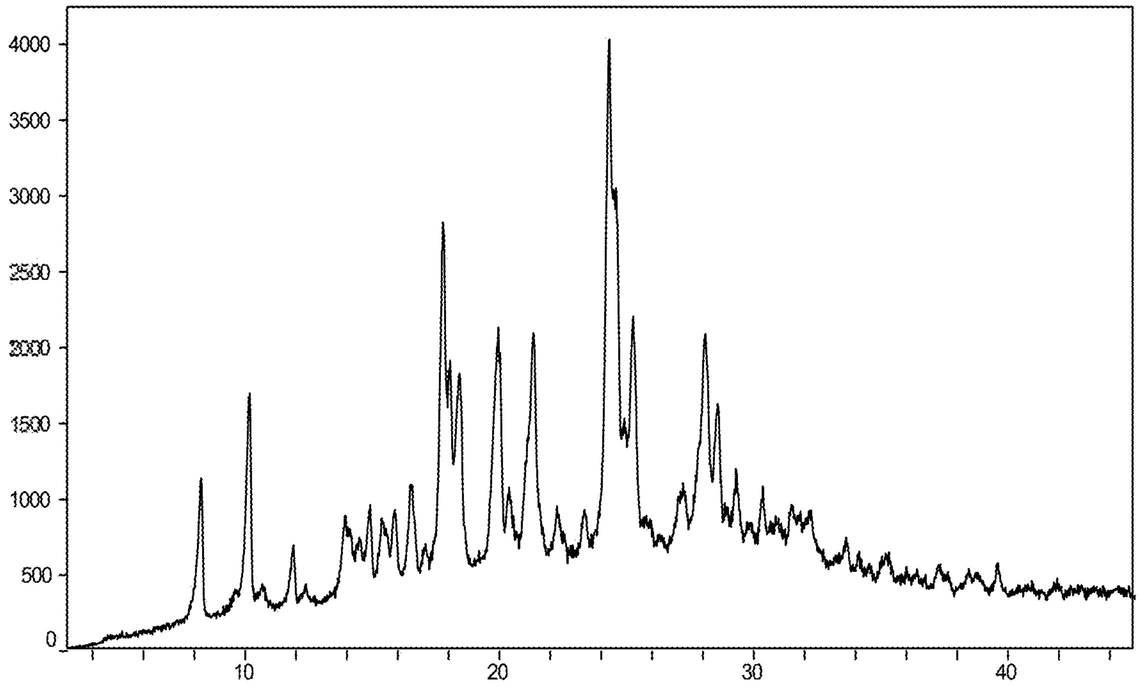
FIG. 2 shows an X-ray powder diffraction pattern of hydrochloride crystalline form II of the compound of formula (I) of the present invention. The abscissa represents the value of 2θ (degrees), and the ordinate represents peak intensity.

About 10 mg of the compound of formula (I) was dissolved in 0.5 mL of ethyl acetate, and 2.35 μL of concentrated hydrochloric acid in 0.1 mL of ethyl acetate was added; the mixture was stirred at room temperature for 3 days and filtered, and the filter cake was dried in a drying oven at 50° C. and subjected to an XRPD analysis. The X-ray powder diffraction pattern is shown in FIG. 2.

Example 3. Preparation of Hydrochloride Crystalline Form III

Figure 3:
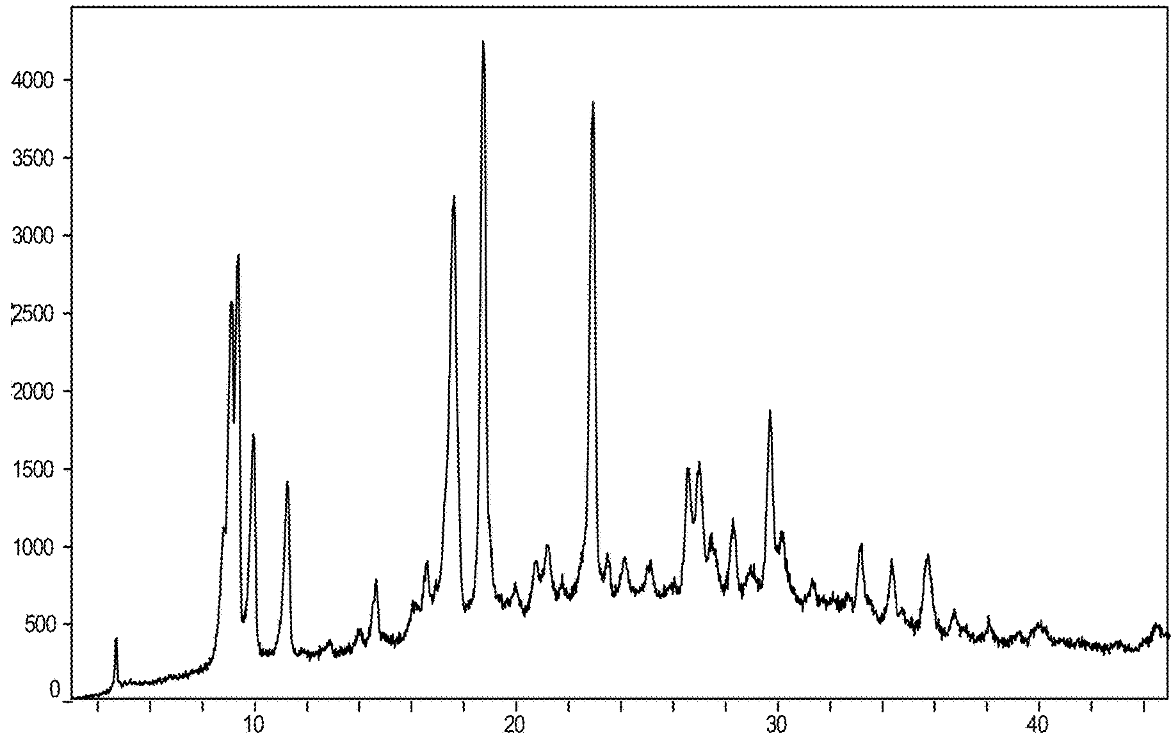
FIG. 3 shows an X-ray powder diffraction pattern of hydrochloride crystalline form III of the compound of formula (I) of the present invention. The abscissa represents the value of 2θ (degrees), and the ordinate represents peak intensity.

About 10 mg of the compound of formula (I) was dissolved in 0.5 mL of acetone, and 2.35 μL of concentrated hydrochloric acid in 0.1 mL of acetone was added; the mixture was stirred at room temperature for 3 days and filtered, and the filter cake was dried in a drying oven at 50° C. and subjected to an XRPD analysis. The X-ray powder diffraction pattern is shown in FIG. 3.

Example 4. Preparation of Hydrochloride Crystalline Form I

Figure 14:
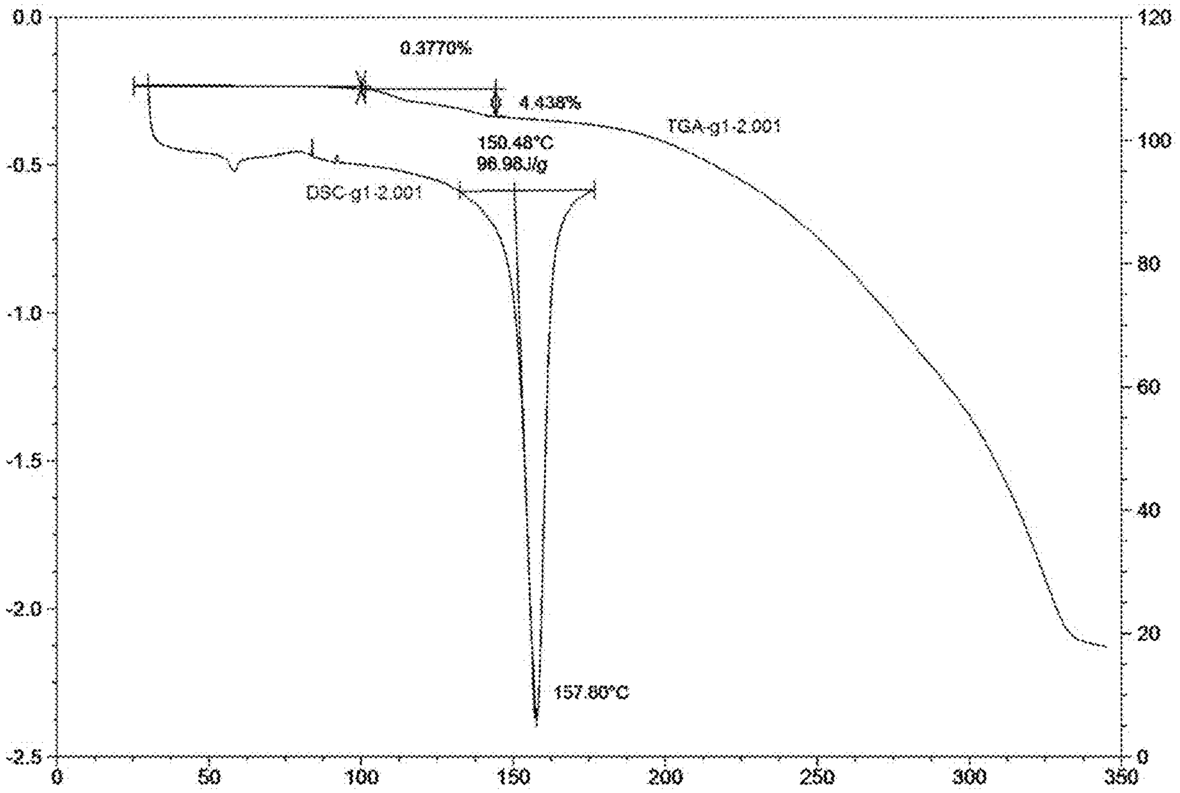
FIG. 14 shows a DSC/TGA graph of hydrochloride crystalline form I of the compound of formula (I) of the present invention. The abscissa represents temperature (° C.), and the ordinate represents heat flow (w/g)/weight (%).
Figure 15:
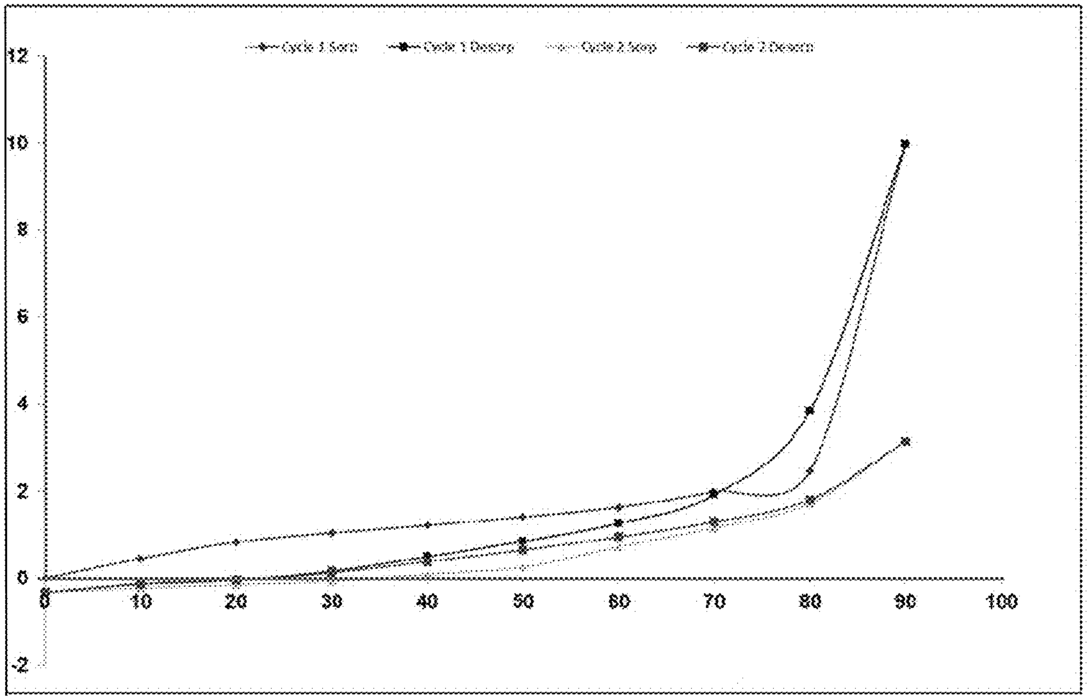
FIG. 15 shows a DVS graph of hydrochloride crystalline form I of the compound of formula (I) of the present invention. The abscissa represents relative humidity (%), and the ordinate represents weight change (%).

About 50 mg of the compound of formula (I) was dissolved in 1.2 mL of methyl tert-butyl ether, and 11.7 μL of concentrated hydrochloric acid in 1.2 mL of methyl tert-butyl ether was added; the mixture was stirred at room temperature for 7 days and filtered, and the filter cake was dried in a drying oven at 50° C. and subjected to XRPD, DSC, TGA and DVS analyses. The X-ray powder diffraction pattern agrees with what is shown in FIG. 1, and the DSC, TGA and DVS analyses are shown in FIGS. 14-15.

Example 5. Preparation of Sulfate Crystalline Form I

Figure 4:
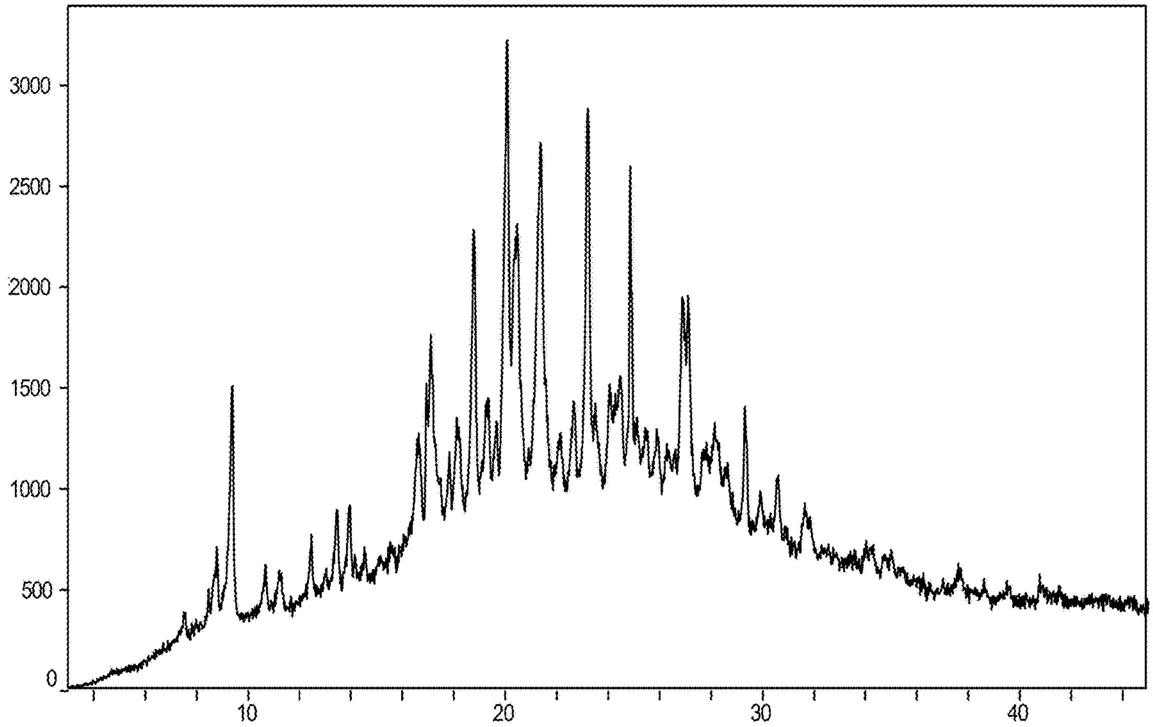
FIG. 4 shows an X-ray powder diffraction pattern of sulfate crystalline form I of the compound of formula (I) of the present invention. The abscissa represents the value of 2θ (degrees), and the ordinate represents peak intensity.

About 10 mg of the compound of formula (I) was dissolved in 0.5 mL of methyl tert-butyl ether, and 4.67 μL of concentrated sulfuric acid in 0.1 mL of methyl tert-butyl ether was added; the mixture was stirred at room temperature for 3 days and filtered, and the filter cake was dried in a drying oven at 50° C. and subjected to an XRPD analysis. The X-ray powder diffraction pattern is shown in FIG. 4.

Example 6. Preparation of Phosphate Crystalline Form I

Figure 5:
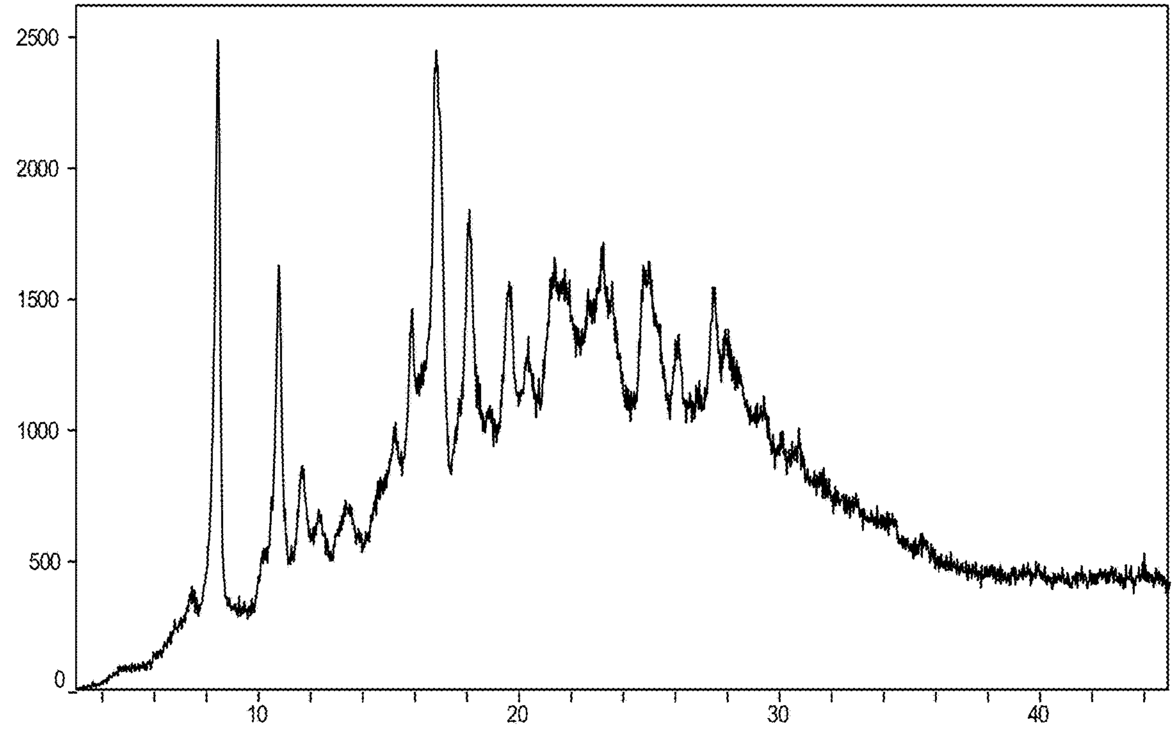
FIG. 5 shows an X-ray powder diffraction pattern of phosphate crystalline form I of the compound of formula (I) of the present invention. The abscissa represents the value of 2θ (degrees), and the ordinate represents peak intensity.

About 10 mg of the compound of formula (I) was dissolved in 0.5 mL of methanol, and 2.74 μL of concentrated phosphoric acid in 0.1 mL of methanol was added; the mixture was stirred, left to stand at −20° C. for 3 days and filtered, and the filter cake was dried in a drying oven at 50° C. and subjected to an XRPD analysis. The X-ray powder diffraction pattern is shown in FIG. 5.

Example 7. Preparation of Phosphate Crystalline Form II

Figure 6:
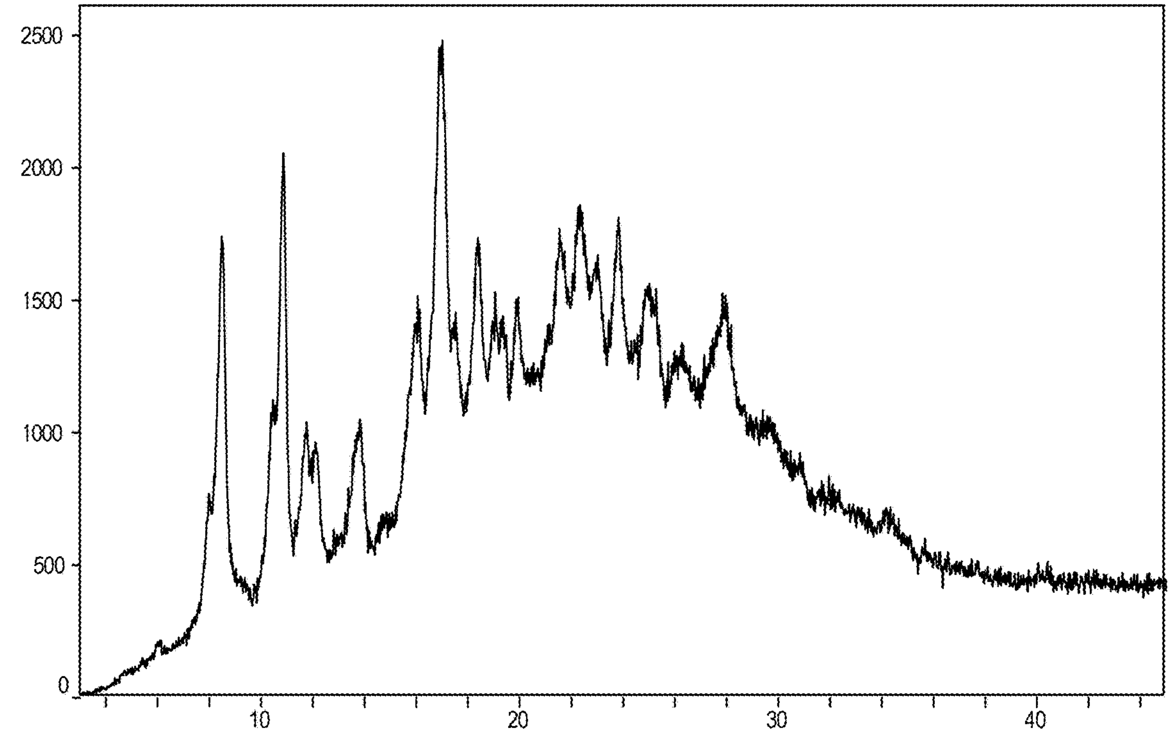
FIG. 6 shows an X-ray powder diffraction pattern of phosphate crystalline form II of the compound of formula (I) of the present invention. The abscissa represents the value of 2θ (degrees), and the ordinate represents peak intensity.

About 10 mg of the compound of formula (I) was dissolved in 0.5 mL of ethyl acetate, and 2.74 μL of concentrated phosphoric acid in 0.1 mL of ethyl acetate was added; the mixture was stirred, left to stand at −20° C. for 3 days and filtered, and the filter cake was dried in a drying oven at 50° C. and subjected to an XRPD analysis. The X-ray powder diffraction pattern is shown in FIG. 6.

Example 8. Preparation of Phosphate Crystalline form III

Figure 7:
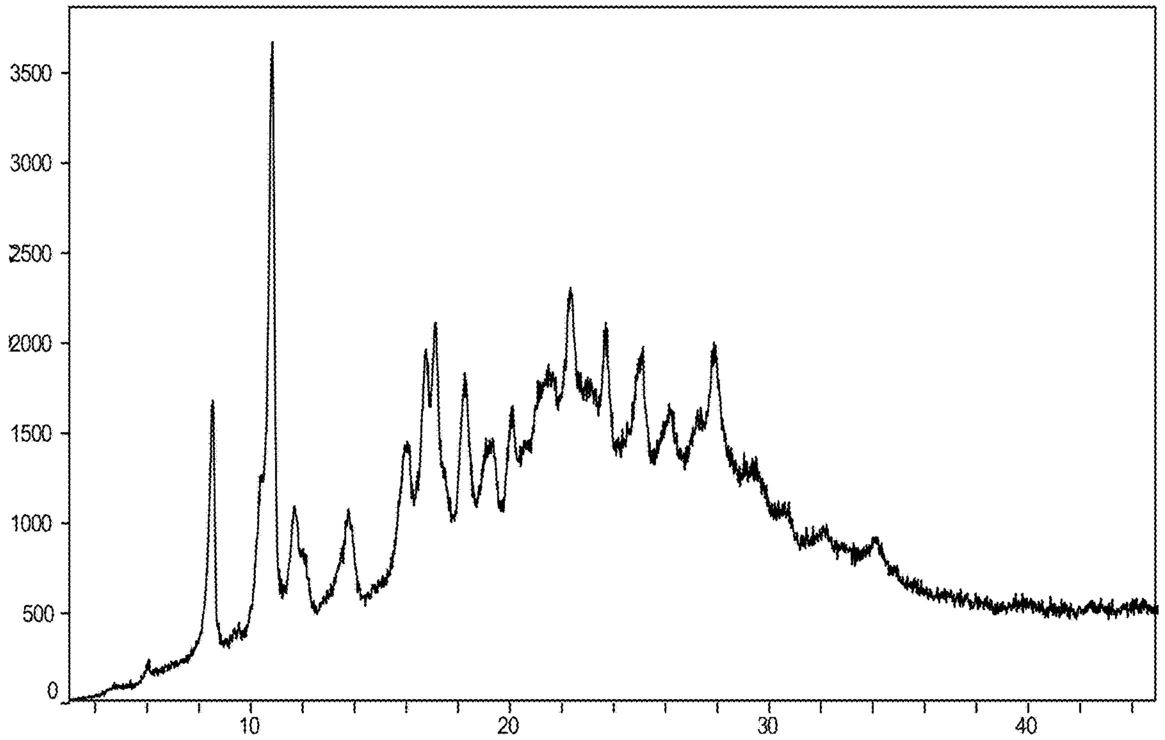
FIG. 7 shows an X-ray powder diffraction pattern of phosphate crystalline form III of the compound of formula (I) of the present invention. The abscissa represents the value of 2θ (degrees), and the ordinate represents peak intensity.

About 10 mg of the compound of formula (I) was dissolved in 0.5 mL of 96% ethanol, and 2.74 μL of concentrated phosphoric acid in 0.1 mL of 96% ethanol was added; the mixture was stirred, left to stand at −20° C. for 3 days and filtered, and the filter cake was dried in a drying oven at 50° C. and subjected to an XRPD analysis. The X-ray powder diffraction pattern is shown in FIG. 7.

Example 9. Preparation of Phosphate Crystalline Form I

Figure 16:
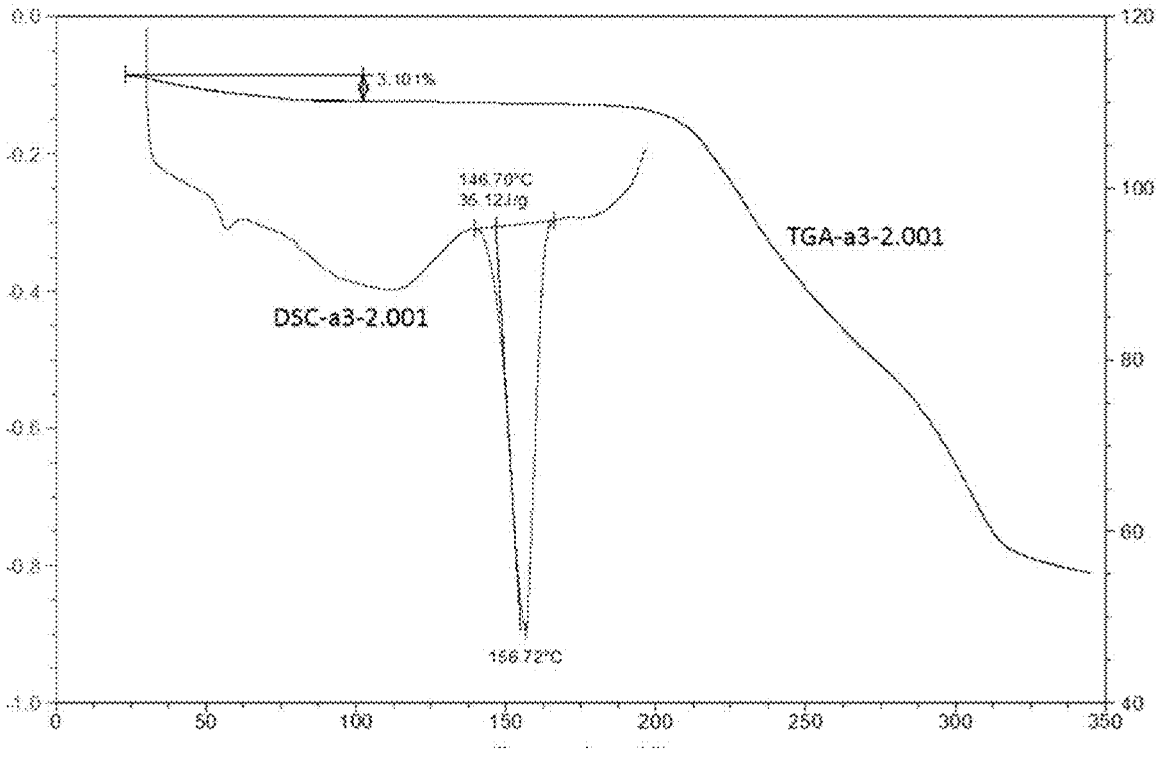
FIG. 16 shows a DSC/TGA graph of phosphate crystalline form I of the compound of formula (I) of the present invention. The abscissa represents temperature (° C.), and the ordinate represents heat flow (w/g)/weight (%).
Figure 17:
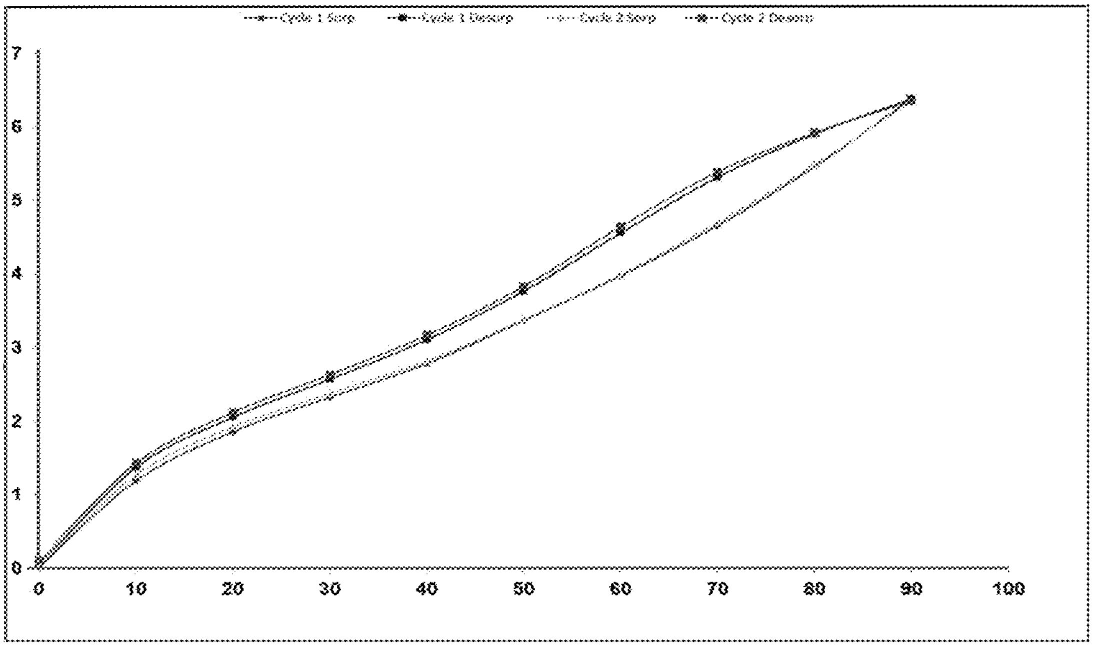
FIG. 17 shows a DVS graph of phosphate crystalline form I of the compound of formula (I) of the present invention. The abscissa represents relative humidity (%), and the ordinate represents weight change (%).

About 50 mg of the compound of formula (I) was dissolved in 1.2 mL of methanol, and 13.7 μL of concentrated phosphoric acid in 1.2 mL of methanol was added; the mixture was stirred, left to stand at −20° C. for 7 days and filtered, and the filter cake was dried in a drying oven at 50° C. and subjected to XRPD, DSC, TGA and DVS analyses. The X-ray powder diffraction pattern is shown in FIG. 5, and the DSC, TGA and DVS analyses are shown in FIGS. 16-17.

Example 10. Preparation of Methanesulfonate Crystalline Form I

Figure 8:
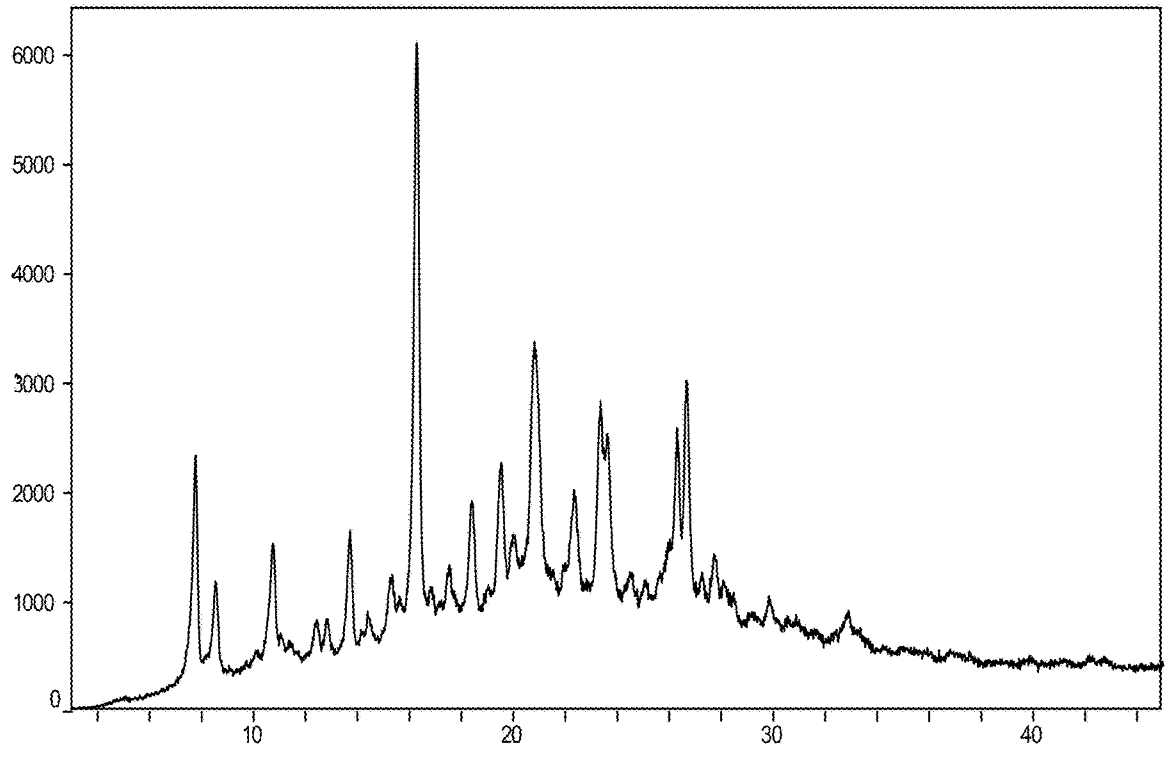
FIG. 8 shows an X-ray powder diffraction pattern of methanesulfonate crystalline form I of the compound of formula (I) of the present invention. The abscissa represents the value of 2θ (degrees), and the ordinate represents peak intensity.

About 10 mg of the compound of formula (I) was dissolved in 0.5 mL of tetrahydrofuran, and 2.29 μL of methanesulfonic acid in 0.1 mL of tetrahydrofuran was added; the mixture was stirred, left to stand at −20° C. for 3 days and filtered, and the filter cake was dried in a drying oven at 50° C. and subjected to an XRPD analysis. The X-ray powder diffraction pattern is shown in FIG. 8.

Example 11. Preparation of Methanesulfonate Crystalline Form II

Figure 9:
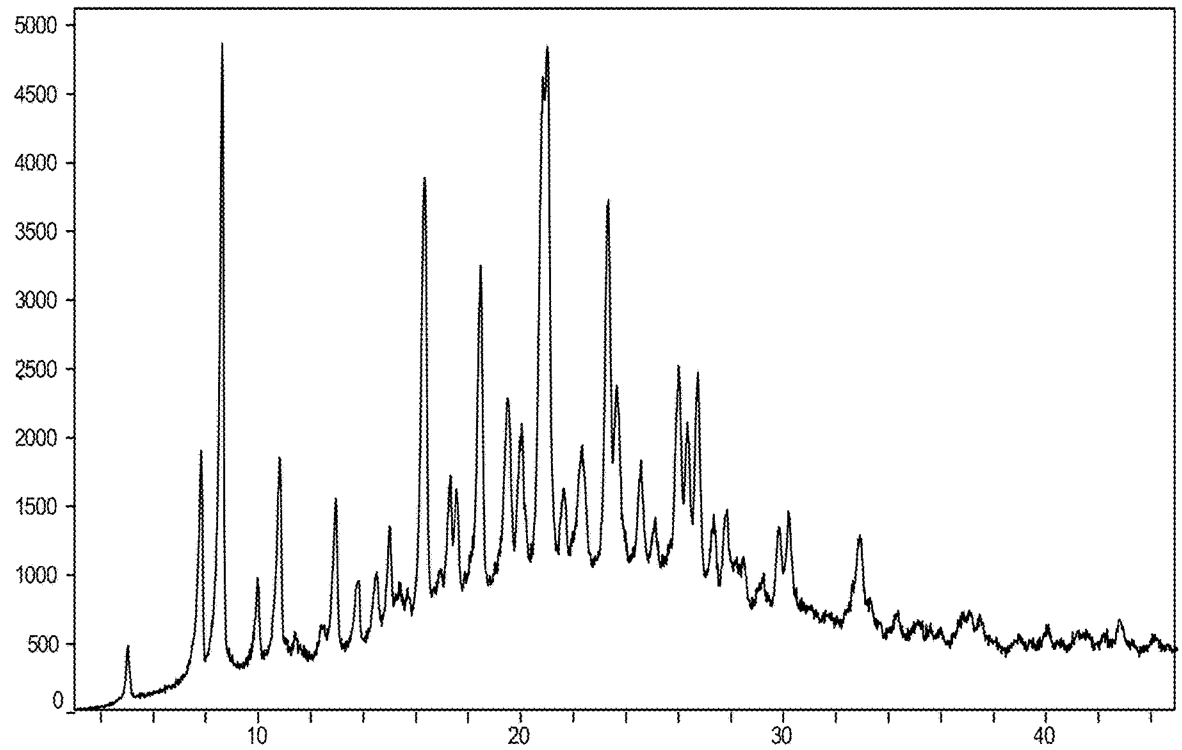
FIG. 9 shows an X-ray powder diffraction pattern of methanesulfonate crystalline form II of the compound of formula (I) of the present invention. The abscissa represents the value of 2θ (degrees), and the ordinate represents peak intensity.

About 10 mg of the compound of formula (I) was dissolved in 0.5 mL of acetone, and 2.29 μL of methanesulfonic acid in 0.1 mL of acetone was added; the mixture was stirred, left to stand at −20° C. for 3 days and filtered, and the filter cake was dried in a drying oven at 50° C. and subjected to an XRPD analysis. The X-ray powder diffraction pattern is shown in FIG. 9.

Example 12. Preparation of Methanesulfonate Crystalline Form II

Figure 18:
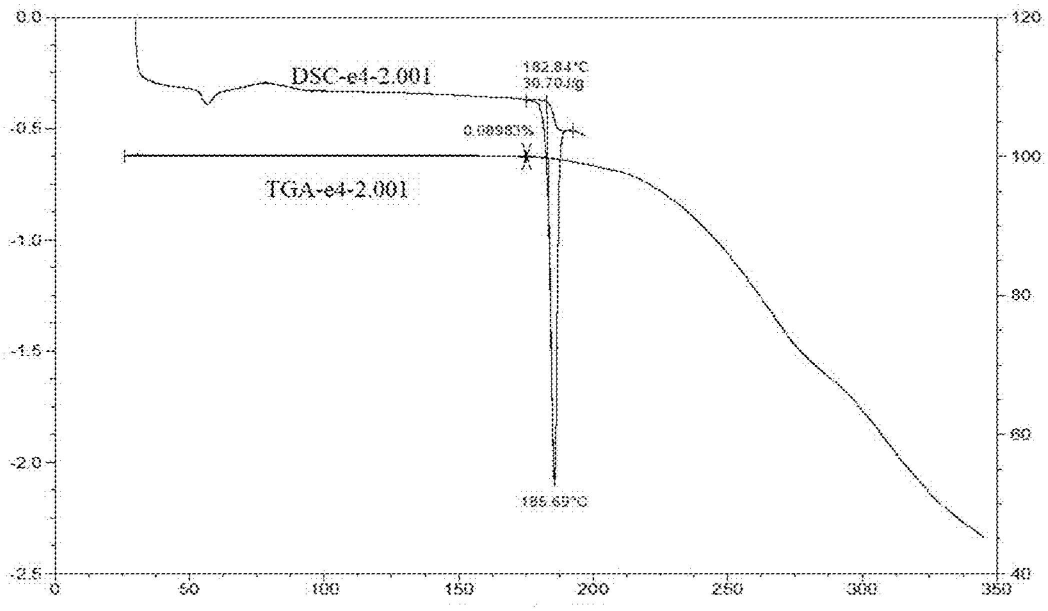
FIG. 18 shows a DSC/TGA graph of methanesulfonate crystalline form II of the compound of formula (I) of the present invention. The abscissa represents temperature (° C.), and the ordinate represents heat flow (w/g)/weight (%).
Figure 19:
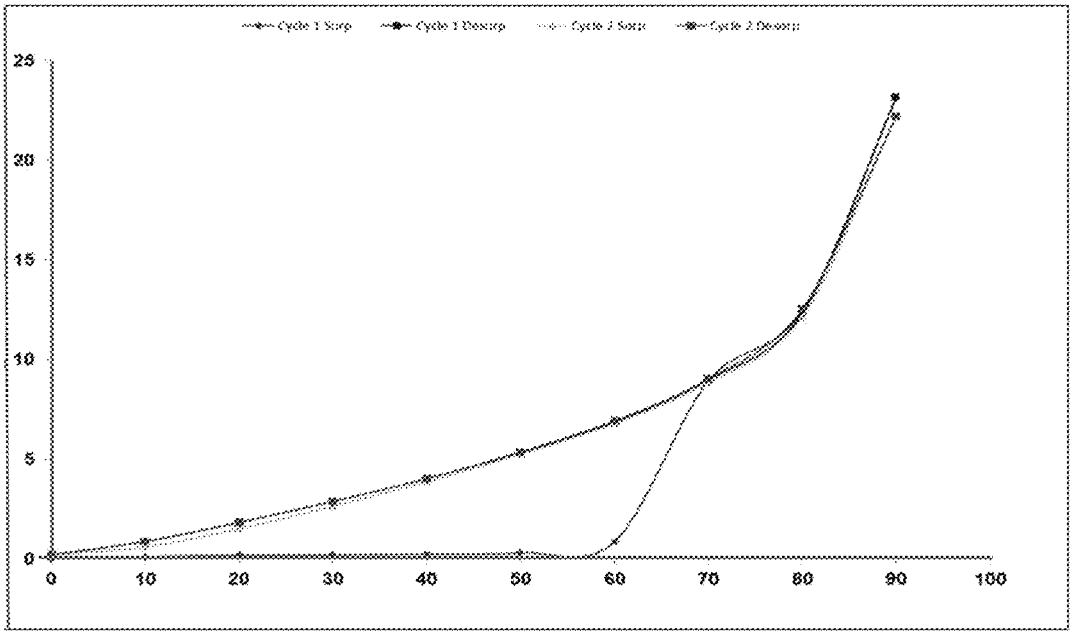
FIG. 19 shows a DVS graph of methanesulfonate crystalline form II of the compound of formula (I) of the present invention. The abscissa represents relative humidity (%), and the ordinate represents weight change (%).

About 50 mg of the compound of formula (I) was dissolved in 1.2 mL of acetone, and 11.4 μL of methanesulfonic acid in 1.2 mL of acetone was added; the mixture was stirred, left to stand at −5° C. for 3 days and filtered, and the filter cake was dried in a drying oven at 50° C. and subjected to XRPD, DSC, TGA and DVS analyses. The X-ray powder diffraction pattern is shown in FIG. 9, and the DSC, TGA and DVS analyses are shown in FIGS. 18-19.

Example 13. Preparation of Citrate Crystalline Form I

Figure 10:
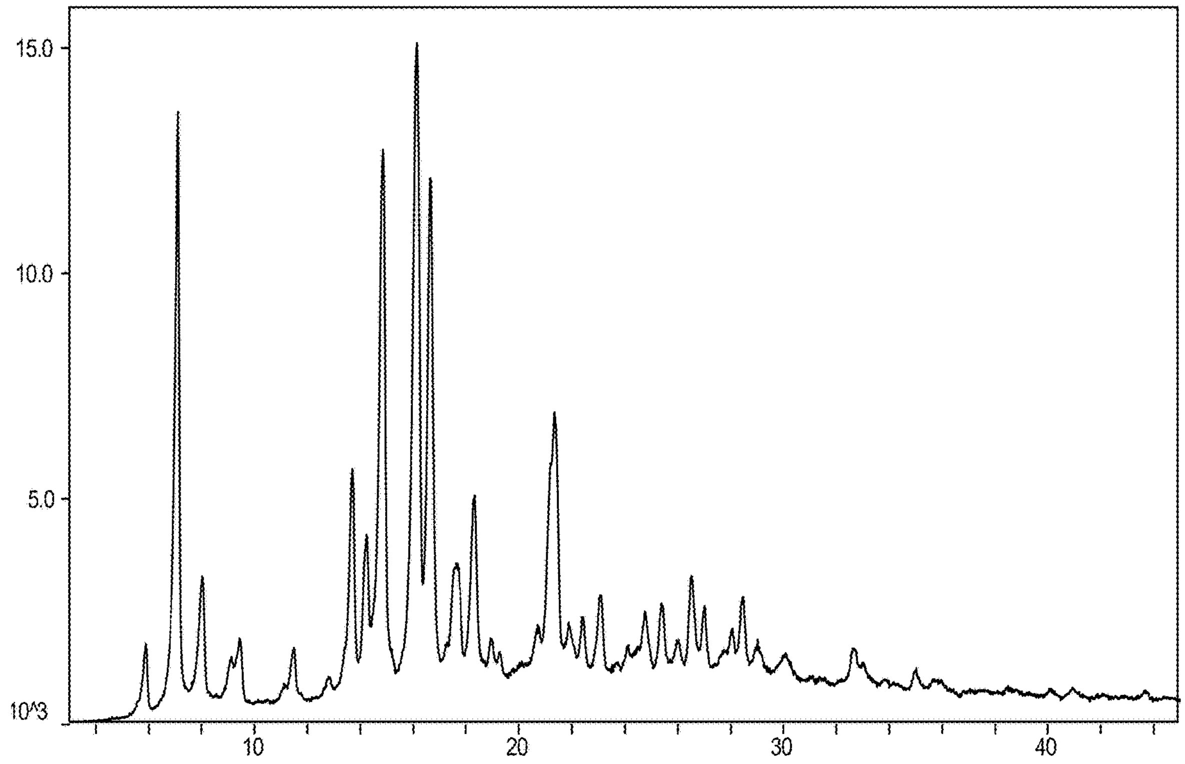

About 10 mg of the compound of formula (I) was dissolved in 0.5 mL of acetonitrile, and 4.57 mg of citric acid was added; the mixture was stirred at room temperature for 3 days and filtered, and the filter cake was dried in a drying oven at 50° C. and subjected to an XRPD analysis. The X-ray powder diffraction pattern is shown in FIG. 10.

Example 14. Preparation of Malate Crystalline Form I

Figure 11:
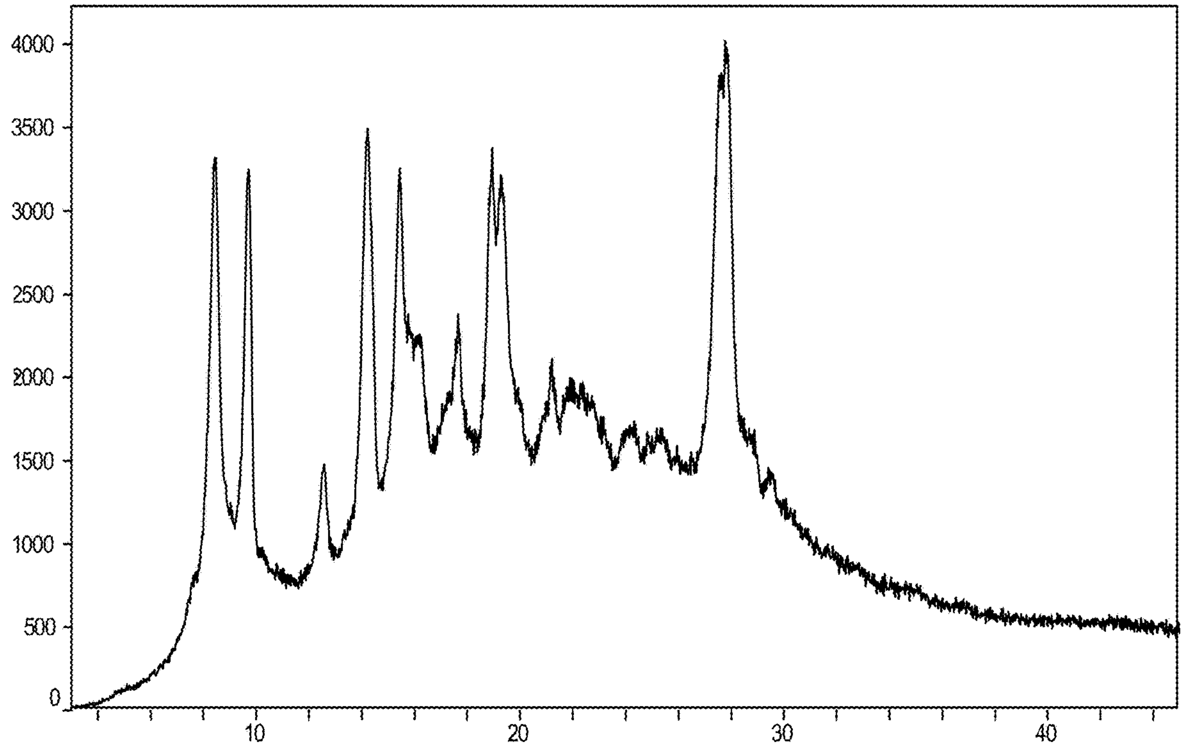
FIG. 11 shows an X-ray powder diffraction pattern of malate crystalline form I of the compound of formula (I) of the present invention. The abscissa represents the value of 2θ (degrees), and the ordinate represents peak intensity.

About 10 mg of the compound of formula (I) was dissolved in 0.5 mL of ethyl acetate, and 2.76 mg of malic acid was added; the mixture was stirred at room temperature for 3 days and filtered, and the filter cake was dried in a drying oven at 50° C. and subjected to an XRPD analysis. The X-ray powder diffraction pattern is shown in FIG. 11.

Example 15. Preparation of Tartrate Crystalline Form I

Figure 12:
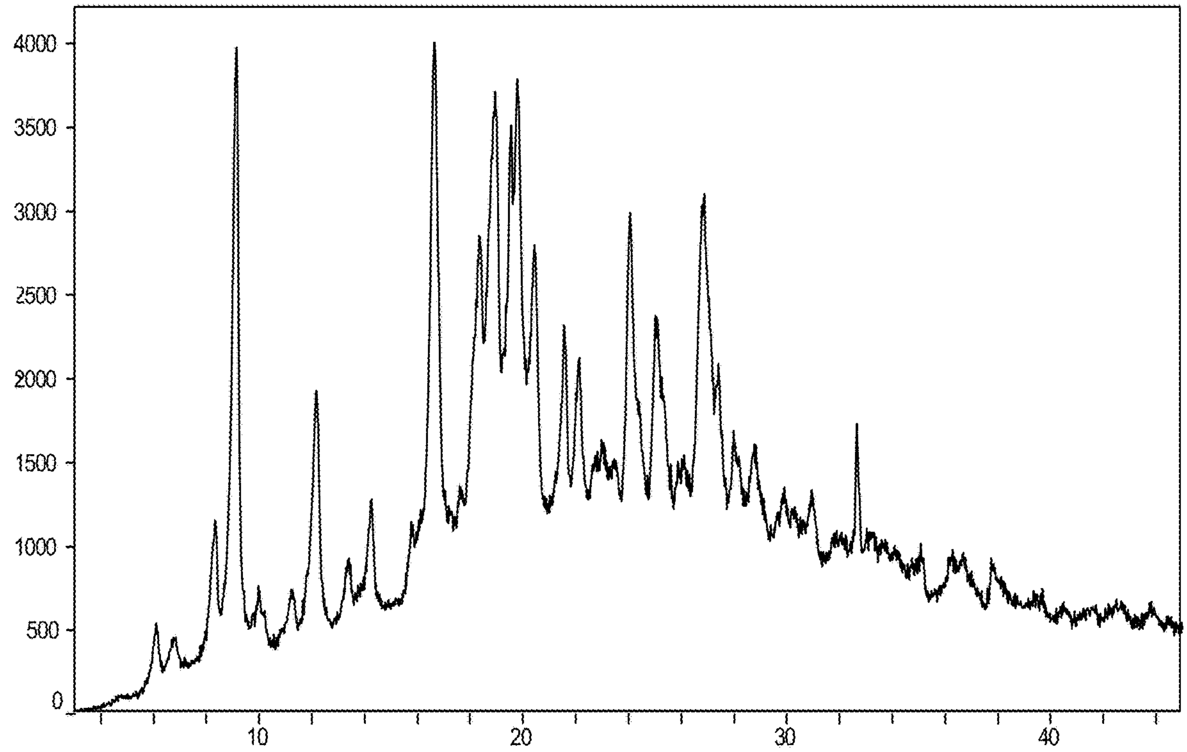
FIG. 12 shows an X-ray powder diffraction pattern of tartrate crystalline form I of the compound of formula (I) of the present invention. The abscissa represents the value of 2θ (degrees), and the ordinate represents peak intensity.

About 10 mg of the compound of formula (I) was dissolved in 0.5 mL of acetonitrile, and 3.57 mg of tartaric acid was added; the mixture was stirred, the solvent was volatilized, and the solid was dried in a drying oven at 50° C. and subjected to an XRPD analysis. The X-ray powder diffraction pattern is shown in FIG. 12.

Example 16. Preparation of Tartrate Crystalline Form I

Figure 20:
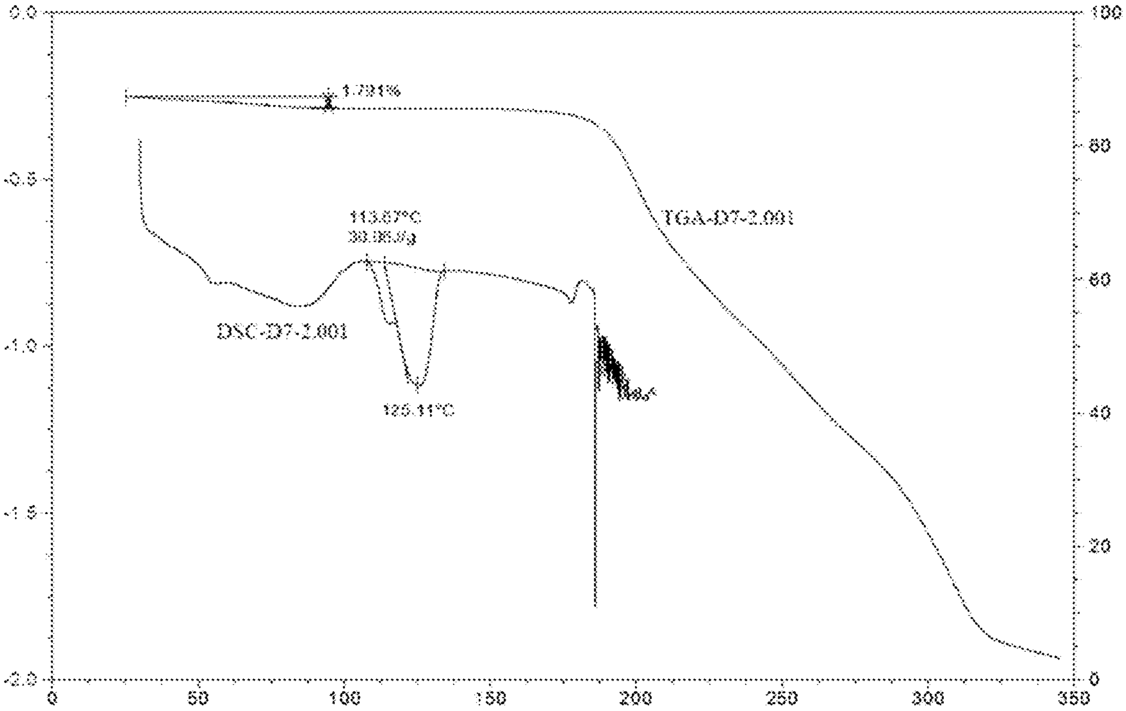
FIG. 20 shows a DSC/TGA graph of tartrate crystalline form I of the compound of formula (I) of the present invention. The abscissa represents temperature (° C.), and the ordinate represents heat flow (w/g)/weight (%).
Figure 21:
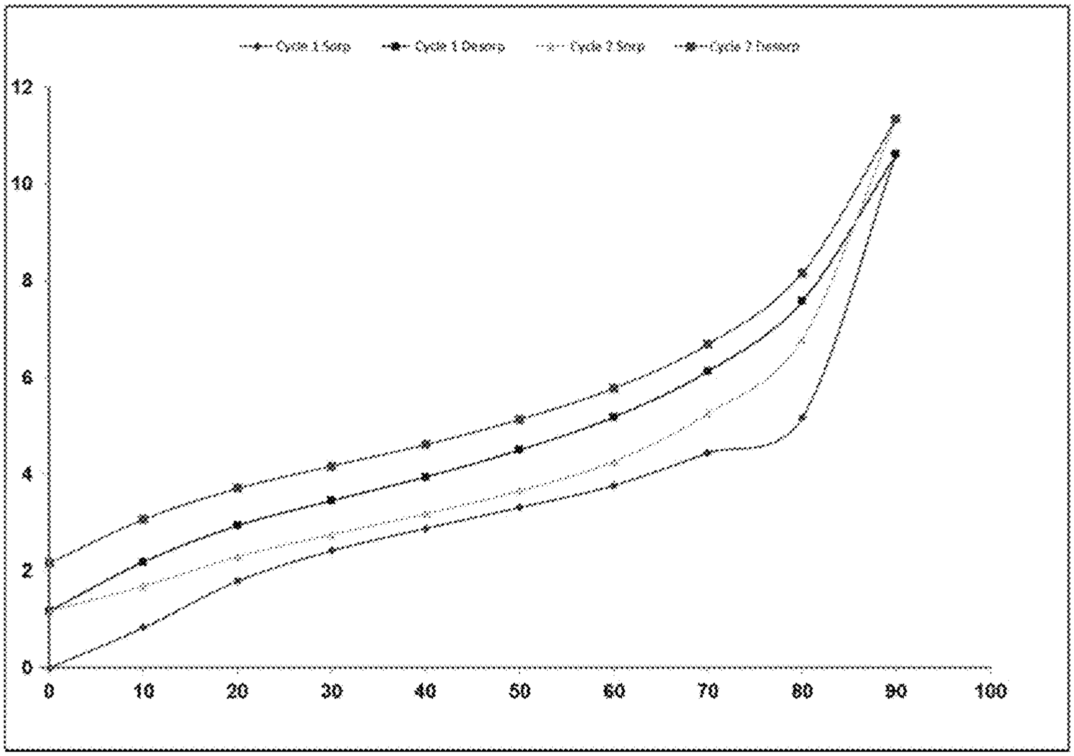
FIG. 21 shows a DVS graph of tartrate crystalline form I of the compound of formula (I) of the present invention. The abscissa represents relative humidity (%), and the ordinate represents weight change (%).

About 50 mg of the compound of formula (I) was dissolved in 1.2 mL of acetonitrile, and 17.87 mg of tartaric acid, 1 mL of acetonitrile and 0.2 mL of purified water were added; the mixture was stirred, and no precipitate was produced; the mixture was left to stand at 5° C. for one week, and no precipitate was produced; 1 mL of methyl tert-butyl ether was added; the mixture was stirred, left to stand at −20° C. for one week and filtered, and the filter cake was dried in a drying oven at 50° C. and subjected to XRPD, DSC, TGA and DVS analyses. The X-ray powder diffraction pattern is shown in FIG. 12, and the DSC, TGA and DVS analyses are shown in FIGS. 20-21.

Example 17. Preparation of Fumarate Crystalline Form I

Figure 13:
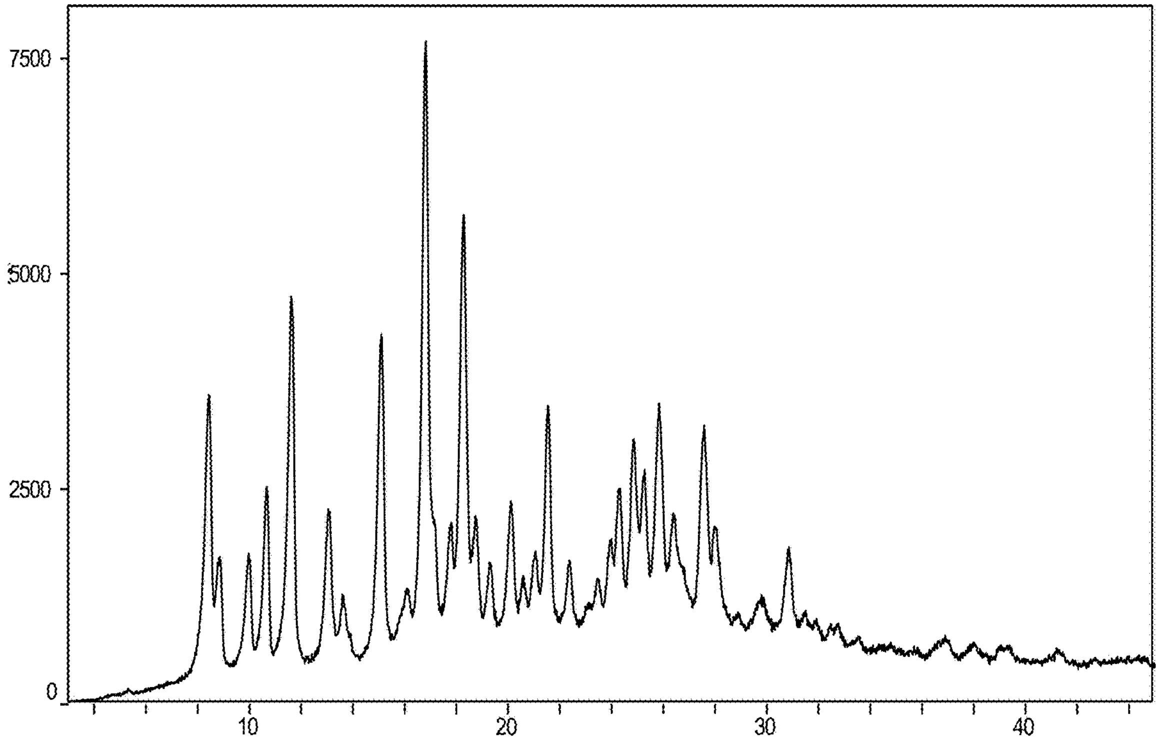
FIG. 13 shows an X-ray powder diffraction pattern of fumarate crystalline form I of the compound of formula (I) of the present invention. The abscissa represents the value of 2θ (degrees), and the ordinate represents peak intensity.

About 10 mg of the compound of formula (I) was dissolved in 0.5 mL of methyl tert-butyl ether, and 2.76 mg of fumaric acid was added; the mixture was stirred, left to stand at −20° C. for 3 days and filtered, and the filter cake was dried in a drying oven at 50° C. and subjected to an XRPD analysis. The X-ray powder diffraction pattern is shown in FIG. 13.

Example 18. Analysis of Structure of Hydrochloride Crystalline Form I 40 mg of the compound of formula (I) was weighed out into a 20 mL vial, 3 mL of acetone was added to dissolve it, and 40 µL of concentrated hydrochloric acid (12 M) was added to obtain a suspension. The suspension was filtered through a syringe filter made of FPTE with a pore size of 0.22 m to obtain a clear solution. 0.2 mL of the filtrate was placed into a 2 mL vial, the vial was sealed with a sealing film, and small holes were formed in the sealing film; the filtrate was slowly volatilized at room temperature to obtain a flaky-shaped single crystal with a small volume as a seed crystal.

40 mg of the compound of formula (I) was weighed out into a 20 mL vial, 3 mL of acetone was added to dissolve it, and 40 µL of concentrated hydrochloric acid (12 M) was added to obtain a suspension. The suspension was filtered through a syringe filter made of FPTE with a pore size of 0.22 m to obtain a clear solution. 0.4 mL of the filtrate was placed into a 2 mL vial, 0.3 mL of acetone was then added, and a small amount of the prepared flaky-shaped seed crystal was added; the vial was sealed with a sealing film, and small holes were formed in the sealing film; the filtrate was slowly volatilized at room temperature to obtain a flaky-shaped single crystal with a small volume.

Figure 22:
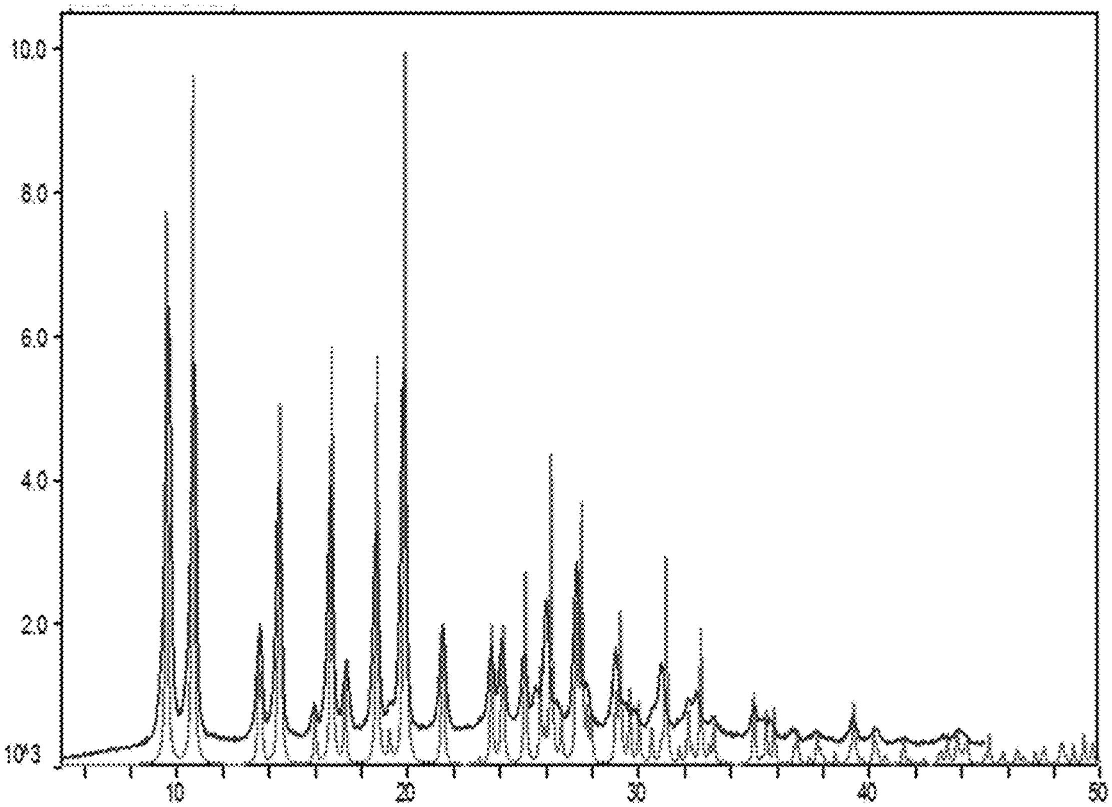
FIG. 22 shows an overlay of a simulated pattern (lower) of a single crystal of the hydrochloride of the compound of formula (I) of the present invention and the X-ray powder diffraction pattern (upper) of hydrochloride crystalline form I. The abscissa represents the value of 2θ (degrees), and the ordinate represents peak intensity.
Figure 23:
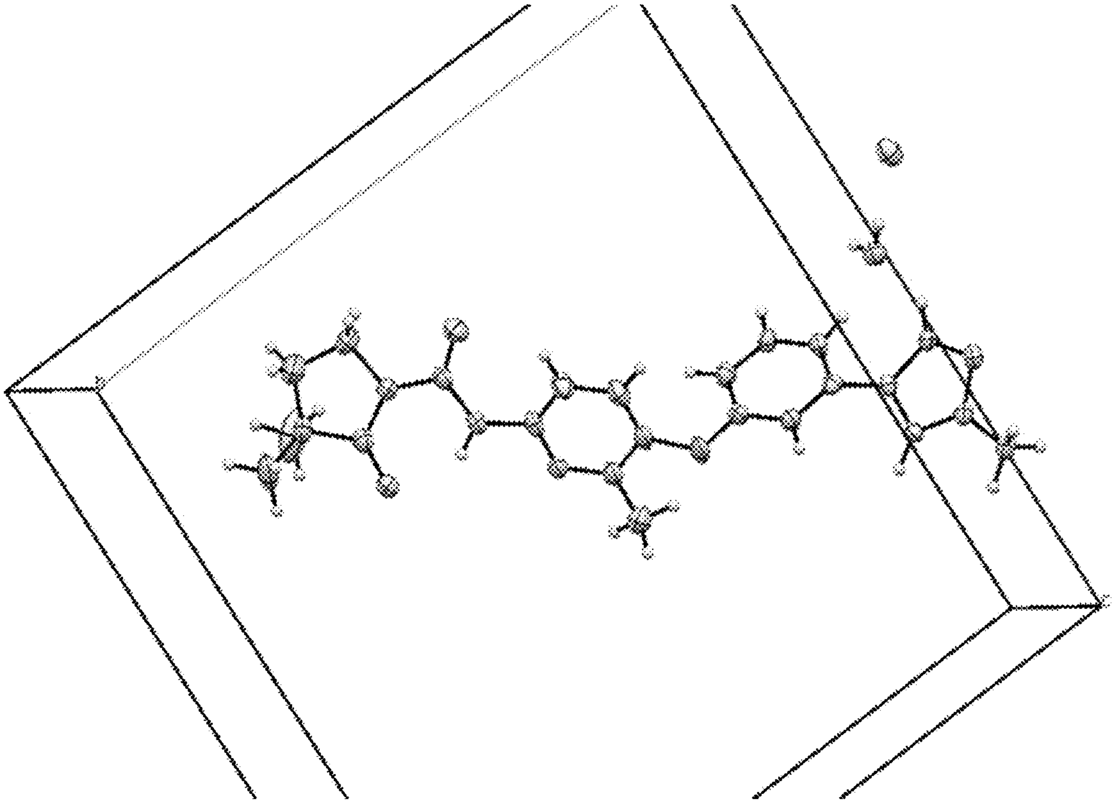
FIG. 23 shows the structure of a unit cell of a single crystal of hydrochloride crystalline form I of the compound of formula (I) of the present invention.

A proper single crystal was selected for analysis on a Bruker APEX-II CCD single-crystal diffractometer. The temperature was maintained at 220 K during data collection. A powder diffraction pattern was simulated from the single-crystal diffraction pattern by calculation using Mercury 3.10.2 (Build 189770) software and compared with the powder diffraction pattern of hydrochloride crystalline form I of the compound of formula (I), as shown in FIG. 22. It can be seen from the comparison that the powder diffraction pattern of hydrochloride crystalline form I agrees with the simulated pattern of the single crystal, and no other peaks are shown, which indicates that hydrochloride crystalline form I of the compound of formula (I) of the present patent is a pure phase. It can also be confirmed that hydrochloride crystalline form I of the compound of formula (I) is a monohydrochloride monohydrate. The structure of a unit cell of the single crystal is shown in FIG. 23.

| | |
|---|---|
| Molecular formula: $C_{22}H_{27}ClN_6O_4$ | Z = 4 |
| $M_r$ = 474.94 | F(000) = 1000.0 |
| Space group, Pca21 | Density $D_x$ = 1.338 Mg $m^{-3}$ |
| a = 6.910 (3) Å | Mo K radiation, = 0.71073 Å |
| b = 18.483 (6) Å | Linear absorption coefficient = 0.203 $mm^{-1}$ |
| c = 18.463 (7) Å | Test temperature T = 220 K |
| Unit cell volume V = 2358.0 (15) $Å^3$ | Size of single crystal: 0.22 × 0.2 × 0.05 mm |

Example 19. Solubility Determination

About 2 mg of each of the various crystalline acidic salts and the compound of formula (I) in free form was precisely weighed out into a 2 mL glass vial, and about 100 µL of deionized water was added each time; the mixture was ultrasonicated, and if the compound was not dissolved, the step of adding deionized water and performing ultrasonication was repeated until the compound was completely dissolved or the concentration was <0.2 mg/mL. The total volume of the water added was recorded, the dissolution behavior and result were observed, and the solubility of each compound was calculated. The solubility test results are shown in the table below:

| Crystalline form | Preparation method | Solubility S | Dissolution result |
|---|---|---|---|
| Hydrochloride crystalline form I | Example 4 | S > 20 mg/mL | Clear solution |
| Sulfate crystalline form I | Example 5 | S > 20 mg/mL | Clear solution |
| Phosphate crystalline form I | Example 9 | S > 20 mg/mL | Clear solution |

-continued

| Crystalline form | Preparation method | Solubility S | Dissolution result |
|---|---|---|---|
| Methanesulfonate crystalline form II | Example 12 | S > 20 mg/mL | Clear solution |
| Citrate crystalline form I | Example 13 | S > 20 mg/mL | Clear solution |
| Malate crystalline form I | Example 14 | S > 20 mg/mL | Clear solution |
| Tartrate crystalline form I | Example 16 | S > 20 mg/mL | Clear solution |
| Fumarate crystalline form I | Example 17 | S > 20 mg/mL | Clear solution |
| Compound in free form | API starting material | S < 1.5 mg/mL | Not clear |

It can be seen from the above experimental results that after the compound of formula (I) in free form was salified to obtain the crystalline compounds, the solubility of all the salt forms in water was greatly improved and can satisfy the needs of clinical medicament formulation development. Therefore, after the compound of formula (I) in free form was salified to obtain the crystalline compounds, its solubility and medicament release behavior could be significantly improved.

Example 20. Hygroscopic Behavior Test

The inventors of the present invention measured the hygroscopic weight gains of each of the various crystalline forms in various relative humidity conditions (hygroscopic weight gain/pre-hygroscopic weight*1000%) according to the dynamic vapor sorption method, and assessed the hygroscopicity of the different crystalline compounds. The results are shown in the table below:

| | Hygroscopic weight gain % Relative humidity % | | | | | | | | | |
|---|---|---|---|---|---|---|---|---|---|---|
| Each crystalline form | 0.0 | 10.0 | 20.0 | 30.0 | 40.0 | 50.0 | 60.0 | 70.0 | 80.0 | 90.0 |
| Hydrochloride crystalline form I | 0.00 | 0.13 | 0.24 | 0.34 | 0.42 | 0.52 | 0.63 | 0.81 | 1.37 | 19.40 |
| Phosphate crystalline form I | 0.02 | 1.19 | 1.86 | 2.32 | 2.78 | 3.37 | 3.97 | 4.66 | 5.46 | 6.383 |
| Methanesulfonate crystalline form II | 0.00 | 0.11 | 0.18 | 0.20 | 0.24 | 0.31 | 0.88 | 8.93 | 12.44 | 23.15 |
| Tartrate crystalline form I | 0.00 | 0.83 | 1.79 | 2.42 | 2.88 | 3.32 | 3.77 | 4.44 | 5.17 | 10.61 |

The above experimental results show that: when the relative humidity was less than 8000, the hygroscopic weight gain of hydrochloride crystalline form I was less than 10%; the hygroscopicity of the crystal began to slowly increase only when the relative humidity was increased to 80%; the hygroscopicity of the crystal significantly increased only when the relative humidity was increased to 90%. This hygroscopic characteristic of hydrochloride crystalline form I is very much in line with the storage requirements of clinical formulations. The crystal can absorb a large amount of moisture in a high-humidity environment so that the dissolution of the crystal is accelerated, which favors the granulation process of clinical formulations.

Methanesulfonate crystalline form II has similar hygroscopic characteristics to hydrochloride crystalline form I. The only difference is that when the relative humidity is increased to 70%, the hygroscopicity of methanesulfonate crystalline form II will increase significantly. This hygroscopic characteristic is also very much in line with the requirements of the granulation process of clinical formulations.

The hygroscopic characteristic of tartrate crystalline form I is that the hygroscopic weight gain of the crystal substantially increases equally with the relative humidity: a good linear relationship is present. This hygroscopic characteristic will help the inventors develop special formulations in subsequent studies.

Phosphate crystalline form I also has very characteristic hygroscopicity: the hygroscopicity of the crystal in such a crystalline form is always kept at a relatively low level regardless of the ambient relative humidity. This characteristic can be utilized in storage, transport and production in different regions, and also favors the preparation of special formulations.

It is widely known that the hygroscopicity of a medicament is an important physicochemical property which affects the production, storage and content of the medicament. According to different hygroscopic characteristics, different medicament formulations can be developed to meet different requirements of clinical medicament development.

The low-hygroscopicity physical form makes the medicament more stable in production, storage and content. Therefore, the above crystalline compounds all have relatively good hygroscopic characteristics. Particularly, hydrochloride crystalline form I and phosphate crystalline form I have more advantages in developability over other crystalline salts.

All documents mentioned in the present invention are incorporated as references, just as each document is individually cited as a reference. In addition, it should be understood that various modifications or changes may be made by those skilled in the art after reading the above teachings of the present invention, and these equivalent forms also fall within the scope to which the present invention relates.

The invention claimed is:

1. A crystalline hydrochloride salt of a compound of formula (I):

(I)

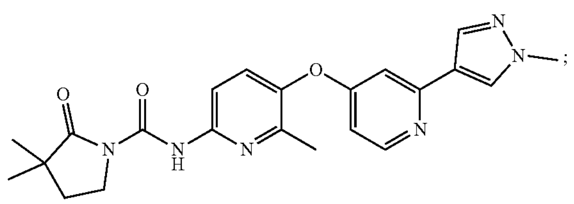

having an X-ray powder diffraction (XRPD) pattern comprising four or more peaks at angles of diffraction (2θ) of 9.52±0.2°, 10.64±0.2°, 14.32±0.2°, 16.56±0.2°, 18.52±0.2°, 19.72±0.2°, and 27.20±0.2°.

2. The crystalline hydrochloride salt of the compound of formula (I) of claim 1, having an X-ray powder diffraction pattern (XRPD) comprising peaks which are substantially identical to those at angles of diffraction (2θ) shown in FIG. 1.

3. The crystalline hydrochloride salt of the compound of formula (I) of claim 1, wherein the crystalline hydrochloride salt of the compound of formula (I) is a monohydrochloride monohydrate.

4. The crystalline hydrochloride salt of the compound of formula (I) of claim 1, having a DSC/TGA graph substantially identical to that shown in FIG. 14.

5. The crystalline hydrochloride salt of the compound of formula (I) of claim 1, having a unit cell measured at Mo K radiation=0.71073 Å and T=220 K as follows:

space group, Pca21;

a=6.910 (3) Å;

b=18.483 (6) Å; and c=18.463 (7) Å.

6. A pharmaceutical composition comprising the crystalline hydrochloride salt of the compound of formula (I) of claim 1 and a pharmaceutically acceptable carrier.

7. A method for preparing the crystalline hydrochloride salt of the compound of formula (I) of claim 1, comprising:

1) Dissolving or dispersing the compound of formula (I) in free base form in a water-containing solvent or a suitable organic solvent, and adding liquid hydrochloric acid; or adding the compound of formula (I) in free base form to a solution of hydrochloric acid; and 2) collecting a solid product precipitated in the above process, or creating a degree of supersaturation to obtain a crystalline product.

8. The method of claim 7, wherein a method of creating the degree of supersaturation in step 2) comprises one or more of: adding a seed crystal, volatizing a solvent, and adding an anti-solvent and cooling.

9. The method of claim 7, wherein the suitable organic solvent is selected from the group consisting of methanol, ethanol, isopropanol, acetonitrile, acetone, tetrahydrofuran, ethyl acetate, methyl tert-butyl ether, mixtures thereof, and aqueous solutions of any of the foregoing.

10. A method for treating a CSP-1R-associated ovarian cancer, pancreatic cancer, prostate cancer, lung cancer, breast cancer, renal carcinoma, liver cancer, cervical cancer, metastatic cancer in bone, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, primary tumor metastasis, myeloproliferative disease, leukemia, rheumatic arthritis, rheumatoid arthritis, osteoarthritis, multiple sclerosis, autoimmune nephritis, lupus, Crohn's disease, asthma, chronic obstructive pulmonary disease, osteoporosis, hypereosinophilic syndrome, mastocytosis or mast cell leukemia, wherein the method comprises administering the crystalline hydrochloride salt of the compound of formula (I) of claim 1 to a subject in need thereof.

* * * * *